US009593350B2

(12) United States Patent
Kim et al.

(10) Patent No.: US 9,593,350 B2
(45) Date of Patent: Mar. 14, 2017

(54) LACTATE DEHYDROGENASE MUTANT, POLYNUCLEOTIDE CODING FOR THE MUTANT, YEAST CELL INCLUDING THE POLYNUCLEOTIDE, METHOD OF PREPARING THE MUTANT, AND METHOD OF PRODUCING THE LACTATE USING THE SAME

(71) Applicant: Samsung Electronics Co., Ltd., Suwon-si, Gyeonggi-do (KR)

(72) Inventors: Ji eun Kim, Suwon-si (KR); So young Lee, Daejeon (KR); Woo yong Lee, Hwaseong-si (KR); Ji yoon Song, Seoul (KR); Seung hyun Lee, Asan-si (KR); Kwang myung Cho, Seongnam-si (KR); Chang duk Kang, Gwacheon-si (KR); Jae young Kim, Suwon-si (KR); Sung soo Kim, Hwaseong-si (KR); Hui-sub Lim, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/622,468

(22) Filed: Feb. 13, 2015

(65) Prior Publication Data

US 2015/0232894 A1 Aug. 20, 2015

(30) Foreign Application Priority Data

Feb. 14, 2014 (KR) ........................ 10-2014-0017517
Sep. 19, 2014 (KR) ........................ 10-2014-0125301

(51) Int. Cl.

| | |
|---|---|
| ***C12N 1/00*** | (2006.01) |
| ***C12N 15/74*** | (2006.01) |
| ***C12P 7/56*** | (2006.01) |
| ***C07H 21/04*** | (2006.01) |
| ***C12N 9/04*** | (2006.01) |

(52) U.S. Cl.

CPC .............. *C12P 7/56* (2013.01); *C12N 9/0006* (2013.01); *C12Y 101/01027* (2013.01); *C12Y 101/01* (2013.01); *Y02P 20/52* (2015.11)

(58) Field of Classification Search

None

See application file for complete search history.

(56) References Cited

U.S. PATENT DOCUMENTS

| | | | |
|---|---|---|---|
| 6,429,006 | B1 | 8/2002 | Porro et al. |
| 7,534,597 | B2 | 5/2009 | Hause et al. |
| 8,039,238 | B2 | 10/2011 | Saito et al. |
| 8,071,357 | B2 | 12/2011 | Sawai et al. |
| 8,097,448 | B2 | 1/2012 | Suominen et al. |
| 2010/0273225 | A1 | 10/2010 | Sawai et al. |
| 2012/0058529 | A1 | 3/2012 | Ikushima et al. |
| 2013/0065284 | A1 | 3/2013 | Chung et al. |

FOREIGN PATENT DOCUMENTS

| | | | |
|---|---|---|---|
| JP | 2006-020602 | B2 | 1/2006 |
| JP | 2008-029329 | A | 2/2008 |
| JP | 2008-283917 | A | 11/2008 |

OTHER PUBLICATIONS

Echigoya et al. Molecular characterization and expression pattern of the equine lactate dehydrogenase., Gene (2009), 447: 40-50.*

Adachi et al. Modification of metabolic pathways of *Saccharomyces cerevisiae* by the expression of lactate dehydrogenase and deletion of pyruvate decarboxylase genes for the lactic acid fermentation at low pH value, J of Fermentation and bioengineering, (1998), 86(3), 284-289.*

Lodi et al. Carbon catabolite repression in Kluyveromyces lactis: isolation and characterization of the of the KIDLD gene encoding the mitochondrial enzyme D-lactae ferricytochrome c oxidoreductase., Mol Gen Genet (1994), 244: 622-629.*

Hondred et al. Hypoxically inducible barley lactate dehydrogenase: cDNA cloning and molecular analysis, Proc. Natl. Acad. Sci. USA vol. 87, p. 7300-7304.*

Branduardi et al., "Lactate production yield from engineered yeasts is dependent from the host background, the lactate dehydrogenase source and the lactate export", *Microbial Cell Factories*, 5(4): 1-12 (2006).

* cited by examiner

*Primary Examiner* — Iqbal H Chowdhury

(74) *Attorney, Agent, or Firm* — Leydig, Voit & Meyer, Ltd.

(57) ABSTRACT

A lactate dehydrogenase mutant, a polynucleotide encoding the mutant, a recombinant yeast cell including the polynucleotide, and a method of preparing the mutant and a method of producing lactate by using the same.

11 Claims, 8 Drawing Sheets

SEQUENCE LISTING

```
<160> NUMBER OF SEQ ID NOS: 63

<210> SEQ ID NO 1
<211> LENGTH: 332
<212> TYPE: PRT
<213> ORGANISM: Bos Taurus

<400> SEQUENCE: 1

Met Ala Thr Leu Lys Asp Gln Leu Ile Gln Asn Leu Leu Lys Glu Glu
  1               5                  10                  15

His Val Pro Gln Asn Lys Ile Thr Ile Val Gly Val Gly Ala Val Gly
             20                  25                  30

Met Ala Cys Ala Ile Ser Ile Leu Met Lys Asp Leu Ala Asp Glu Val
         35                  40                  45

Ala Leu Val Asp Val Met Glu Asp Lys Leu Lys Gly Glu Met Met Asp
     50                  55                  60
```

-continued

```
Leu Gln His Gly Ser Leu Phe Leu Arg Thr Pro Lys Ile Val Ser Gly
 65                 70                  75                  80

Lys Asp Tyr Asn Val Thr Ala Asn Ser Arg Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr His Glu Glu Glu Ala Cys Leu Lys Lys Ser Ala
305                 310                 315                 320

Asp Thr Leu Trp Gly Ile Gln Lys Glu Leu Gln Phe
                325                 330
```

<210> SEQ ID NO 2
<211> LENGTH: 999
<212> TYPE: DNA
<213> ORGANISM: Bos Taurus

<400> SEQUENCE: 2

```
atggcaacat taaaagatca actaatccag aatttgttga aagaggagca tgttccacaa     60

aacaaaatca caatcgtcgg cgtaggtgca gtaggtatgg cttgtgccat atccatcttg    120

atgaaagact tagctgatga ggtcgcgctg gttgatgtaa tggaggacaa acttaaagga    180

gaaatgatgg atcttcaaca tggttcactc tttttgagaa ctcctaaaat tgtatccggg    240

aaagattata acgttaccgc caattctaga cttgttataa tcacggctgg tgcaagacaa    300

caggaaggcg aatcaagact taacttagtt cagagaaacg taaacatttt caagtttatc    360

atcccaaata ttgtaaaata ctccccaaat tgcaagttgc tggttgtttc aaatcctgtt    420

gacatattga cttacgttgc ttggaagatt tcaggtttcc caaagaatag agtaatcgga    480

tctggttgca atctcgattc tgctcgtttt aggtatctga tgggtgaaag attaggggtt    540

catccattga gttgtcacgg atggattcta ggtgaacatg gagatagttc tgtgcctgtt    600
```

-continued

```
tggtcaggtg tcaacgtagc aggtgtctct ttgaaaaatc tacacccaga actaggaaca    660

gatgccgaca aggaacaatg gaaggccgtc cacaaacaag tggtggattc tgcctacgaa    720

gtcatcaaat tgaagggcta cacatcttgg gcaattggct tatccgtcgc tgatctggct    780

gaatcaataa tgaaaaacct ccgtagagtg catcctataa gtactatgat taagggttta    840

tacgggatca aggaagatgt ttttctatct gtgccatgta ttttgggcca aaatggaatt    900

tctgacgttg ttaaagtgac acttactcat gaagaggaag cgtgtttgaa aaagagcgca    960

gacaccttat ggggcatcca aaaggaatta caattctaa                           999


<210> SEQ ID NO 3
<211> LENGTH: 332
<212> TYPE: PRT
<213> ORGANISM: Bos Taurus

<400> SEQUENCE: 3

Met Ala Thr Leu Lys Asp Gln Leu Ile Gln Asn Leu Leu Lys Glu Glu
1               5                   10                  15

His Val Pro Gln Asn Lys Ile Thr Ile Val Gly Val Gly Ala Val Gly
            20                  25                  30

Met Ala Cys Ala Ile Ser Ile Leu Met Lys Asp Leu Ala Asp Glu Val
        35                  40                  45

Ala Leu Val Asp Val Met Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Arg Leu Val Ile Ile Thr Ala
                85                  90                  95

Gly Ala Arg Gln Gln Gly Gly Glu Ser Arg Leu Asn Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300
```

-continued

```
Lys Val Thr Leu Thr His Glu Glu Glu Ala Cys Leu Lys Lys Ser Ala
305                 310                 315                 320

Asp Thr Leu Trp Gly Ile Gln Lys Glu Leu Gln Phe
                325                 330


<210> SEQ ID NO 4
<211> LENGTH: 332
<212> TYPE: PRT
<213> ORGANISM: Bos Taurus

<400> SEQUENCE: 4

Met Ala Thr Leu Lys Asp Gln Leu Ile Gln Asn Leu Leu Lys Glu Glu
  1               5                  10                  15

His Val Pro Gln Asn Lys Ile Thr Ile Val Gly Val Gly Ala Val Gly
             20                  25                  30

Met Ala Cys Ala Ile Ser Ile Leu Met Lys Asp Leu Ala Asp Glu Val
         35                  40                  45

Ala Leu Val Asp Val Met Glu Asp Lys Leu Lys Gly Glu Met Met Asp
     50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Arg Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Gly Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr His Glu Glu Glu Ala Cys Leu Lys Lys Ser Ala
305                 310                 315                 320

Asp Thr Leu Trp Gly Ile Gln Lys Glu Leu Gln Phe
                325                 330
```

<210> SEQ ID NO 5
<211> LENGTH: 332
<212> TYPE: PRT
<213> ORGANISM: Bos Taurus

<400> SEQUENCE: 5

```
Met Ala Thr Leu Lys Asp Gln Leu Ile Gln Asn Leu Leu Lys Glu Glu
  1               5                  10                  15

His Val Pro Gln Asn Lys Ile Thr Ile Val Gly Val Gly Ala Val Gly
             20                  25                  30

Met Ala Cys Ala Ile Ser Ile Leu Met Lys Asp Leu Ala Asp Glu Val
         35                  40                  45

Ala Leu Val Asp Val Met Glu Asp Lys Leu Lys Gly Glu Met Met Asp
     50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Arg Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Asp Gly Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr His Glu Glu Glu Ala Cys Leu Lys Lys Ser Ala
305                 310                 315                 320

Asp Thr Leu Trp Gly Ile Gln Lys Glu Leu Gln Phe
                325                 330
```

<210> SEQ ID NO 6
<211> LENGTH: 999
<212> TYPE: DNA
<213> ORGANISM: Bos Taurus

<400> SEQUENCE: 6

```
atggcaacat taaaagatca actaatacag aatttgttga aagaggagca tgttccacaa     60
```

```
aacaaaatca caatcgtcgg cgtaggtgca gtaggtatgg cttgtgccat atccatcttg    120
atgaaagact tagctgatga ggtcgcgctg gttgatgtaa tggaggacaa acttaaagga    180
gaaatgatgg atcttcaaca tggttcactc tttttgagaa ctcctaaaat tgtatccggg    240
aaagattata acgttaccgc caattctaga cttgttataa tcacggctgg tgcaagacaa    300
cagggaggcg aatcaagact taacttagtt cagagaaacg taaacatttt caagtttatc    360
atcccaaata ttgtaaaata ctccccaaat tgcaagttgc tggttgtttc aaatcctgtt    420
gacatattga cttacgttgc ttggaagatt tcaggtttcc caaagaatag agtaatcgga    480
tctggttgca atctcgattc tgctcgtttt aggtatctga tgggtgaaag attaggggtt    540
catccattga gttgtcacgg atggattcta ggtgaacatg gagatagttc tgtgcctgtt    600
tggtcaggtg tcaacgtagc aggtgtctct ttgaaaaatc tacacccaga actaggaaca    660
gatgccgaca aggaacaatg gaaggccgtc cacaaacaag tggtggattc tgcctacgaa    720
gtcatcaaat tgaagggcta cacatcttgg gcaattggct tatccgtcgc tgatctggct    780
gaatcaataa tgaaaaacct ccgtagagtg catcctataa gtactatgat taagggttta    840
tacgggatca aggaagatgt tttctatct gtgccatgta ttttgggcca aaatggaatt    900
tctgacgttg ttaaagtgac acttactcat gaagaggaag cgtgtttgaa aaagagcgca    960
gacaccttat ggggcatcca aaaggaatta caattctaa                           999
```

<210> SEQ ID NO 7
<211> LENGTH: 999
<212> TYPE: DNA
<213> ORGANISM: Bos Taurus

<400> SEQUENCE: 7

```
atggcaacat taaaagatca actaatacag aatttgttga aagaggagca tgttccacaa     60
aacaaaatca caatcgtcgg cgtaggtgca gtaggtatgg cttgtgccat atccatcttg    120
atgaaagact tagctgatga ggtcgcgctg gttgatgtaa tggaggacaa acttaaagga    180
gaaatgatgg atcttcaaca tggttcactc tttttgagaa ctcctaaaat tgtatccggg    240
aaagattata acgttaccgc caattctaga cttgttataa tcacggctgg tgcaagacaa    300
caggaaggcg aatcaagact taacttagtt cagagaaacg taaacatttt caagtttatc    360
atcccaaata ttgtaaaata ctccccaaat tgcaagttgc tggttgtttc aaatcctgtt    420
gacatattga cttacgttgc ttggaagatt tcaggtttcc caaagaatag agtaatcgga    480
tctggttgca atctcgattc tgctcgtttt aggtatctga tgggtgaaag attaggggtt    540
catccattga gttgtcacgg atggattcta ggtgaacatg gagatagttc tgtgcctgtt    600
tggtcaggtg tcaacgtagc aggtgtctct ttgaaaaatc tacacccaga actaggaaca    660
gatgccgaca aggaacaatg gaaggccgtc cacaaacaag tggtgggttc tgcctacgaa    720
gtcatcaaat tgaagggcta cacatcttgg gcaattggct tatccgtcgc tgatctggct    780
gaatcaataa tgaaaaacct ccgtagagtg catcctataa gtactatgat taagggttta    840
tacgggatca aggaagatgt tttctatct gtgccatgta ttttgggcca aaatggaatt    900
tctgacgttg ttaaagtgac acttactcat gaagaggaag cgtgtttgaa aaagagcgca    960
gacaccttat ggggcatcca aaaggaatta caattctaa                           999
```

<210> SEQ ID NO 8
<211> LENGTH: 999
<212> TYPE: DNA

<213> ORGANISM: Bos Taurus

<400> SEQUENCE: 8

```
atggcaacat taaaagatca actaatacag aatttgttga aagaggagca tgttccacaa     60
aacaaaatca caatcgtcgg cgtaggtgca gtaggtatgg cttgtgccat atccatcttg    120
atgaaagact tagctgatga ggtcgcgctg gttgatgtaa tggaggacaa acttaaagga    180
gaaatgatgg atcttcaaca tggttcactc tttttgagaa ctcctaaaat tgtatccggg    240
aaagattata acgttaccgc caattctaga cttgttataa tcacggctgg tgcaagacaa    300
caggaaggcg aatcaagact taacttagtt cagagaaacg taaacatttt caagtttatc    360
atcccaaata ttgtaaaata ctccccaaat tgcaagttgc tggttgtttc aaatcctgtt    420
gacatattga cttacgttgc ttggaagatt tcaggtttcc caaagaatag agtaatcgga    480
tctggttgca atctcgattc tgctcgtttt aggtatctga tgggtgaaag attaggggtt    540
catccattga gttgtcacgg atggattcta ggtgaacatg gagatagttc tgtgcctgtt    600
tggtcaggtg tcaacgtagc aggtgtctct ttgaaaaatc tacacccaga actaggaaca    660
gatgccgaca aggaacaatg gaaggccgtc cacaaacaag tggtggatgg tgcctacgaa    720
gtcatcaaat tgaagggcta cacatcttgg gcaattggct tatccgtcgc tgatctggct    780
gaatcaataa tgaaaaacct ccgtagagtg catcctataa gtactatgat taagggttta    840
tacgggatca aggaagatgt ttttctatct gtgccatgta ttttgggcca aaatggaatt    900
tctgacgttg ttaaagtgac acttactcat gaagaggaag cgtgtttgaa aaagagcgca    960
gacaccttat ggggcatcca aaaggaatta caattctaa                           999
```

<210> SEQ ID NO 9
<211> LENGTH: 563
<212> TYPE: PRT
<213> ORGANISM: Saccharomyces cerevisiae

<400> SEQUENCE: 9

```
Met Ser Glu Ile Thr Leu Gly Lys Tyr Leu Phe Glu Arg Leu Lys Gln
  1               5                  10                  15

Val Asn Val Asn Thr Val Phe Gly Leu Pro Gly Asp Phe Asn Leu Ser
             20                  25                  30

Leu Leu Asp Lys Ile Tyr Glu Val Glu Gly Met Arg Trp Ala Gly Asn
         35                  40                  45

Ala Asn Glu Leu Asn Ala Ala Tyr Ala Ala Asp Gly Tyr Ala Arg Ile
     50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175
```

```
Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
    530                 535                 540

Ala Pro Gln Asn Leu Val Glu Gln Ala Lys Leu Thr Ala Ala Thr Asn
545                 550                 555                 560

Ala Lys Gln
```

<210> SEQ ID NO 10
<211> LENGTH: 591
<212> TYPE: PRT
<213> ORGANISM: Saccharomyces cerevisiae

<400> SEQUENCE: 10

Met Leu Lys Tyr Lys Pro Leu Leu Lys Ile Ser Lys Asn Cys Glu Ala
1               5                   10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
65                  70                  75                  80

Glu Pro Lys Leu Asp Met Asn Lys Gln Lys Ile Ser Pro Ala Glu Val
                85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu

-continued

```
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
        435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590
```

<210> SEQ ID NO 11
<211> LENGTH: 1692
<212> TYPE: DNA
<213> ORGANISM: Saccharomyces cerevisiae

<400> SEQUENCE: 11

```
atgtctgaaa ttactttggg taaatatttg ttcgaaagat taaagcaagt caacgttaac     60

accgttttcg gtttgccagg tgacttcaac ttgtccttgt tggacaagat ctacgaagtt    120

gaaggtatga gatgggctgg taacgccaac gaattgaacg ctgcttacgc cgctgatggt    180

tacgctcgta tcaagggtat gtcttgtatc atcaccacct tcggtgtcgg tgaattgtct    240

gctttgaacg gtattgccgg ttcttacgct gaacacgtcg gtgttttgca cgttgttggt    300

gtcccatcca tctctgctca agctaagcaa ttgttgttgc accacacctt gggtaacggt    360

gacttcactg ttttccacag aatgtctgcc aacatttctg aaaccactgc tatgatcact    420

gacattgcta ccgccccagc tgaaattgac agatgtatca gaaccactta cgtcacccaa    480

agaccagtct acttaggttt gccagctaac ttggtcgact tgaacgtccc agctaagttg    540

ttgcaaactc caattgacat gtctttgaag ccaaacgatg ctgaatccga aaaggaagtc    600

attgacacca tcttggcttt ggtcaaggat gctaagaacc cagttatctt ggctgatgct    660

tgttgttcca gacacgacgt caaggctgaa actaagaagt tgattgactt gactcaattc    720

ccagctttcg tcaccccaat gggtaagggt tccattgacg aacaacaccc aagatacggt    780

ggtgtttacg tcggtacctt gtccaagcca gaagttaagg aagccgttga atctgctgac    840

ttgattttgt ctgtcggtgc tttgttgtct gatttcaaca ccggttcttt ctcttactct    900

tacaagacca agaacattgt cgaattccac tccgaccaca tgaagatcag aaacgccact    960

ttcccaggtg tccaaatgaa attcgttttg caaaagttgt tgaccactat tgctgacgcc   1020

gctaagggtt acaagccagt tgctgtccca gctagaactc cagctaacgc tgctgtccca   1080
```

```
gcttctaccc cattgaagca agaatggatg tggaaccaat tgggtaactt cttgcaagaa   1140
ggtgatgttg tcattgctga aaccggtacc tccgctttcg gtatcaacca aaccactttc   1200
ccaaacaaca cctacggtat ctctcaagtc ttatggggtt ccattggttt caccactggt   1260
gctaccttgg gtgctgcttt cgctgctgaa gaaattgatc caaagaagag agttatctta   1320
ttcattggtg acggttcttt gcaattgact gttcaagaaa tctccaccat gatcagatgg   1380
ggcttgaagc catacttgtt cgtcttgaac aacgatggtt acaccattga aaagttgatt   1440
cacggtccaa aggctcaata caacgaaatt caaggttggg accacctatc cttgttgcca   1500
actttcggtg ctaaggacta tgaaacccac agagtcgcta ccaccggtga atgggacaag   1560
ttgacccaag acaagtcttt caacgacaac tctaagatca gaatgattga aatcatgttg   1620
ccagtcttcg atgctccaca aaacttggtt gaacaagcta agttgactgc tgctaccaac   1680
gctaagcaat aa                                                        1692
```

<210> SEQ ID NO 12
<211> LENGTH: 1776
<212> TYPE: DNA
<213> ORGANISM: Saccharomyces cerevisiae

<400> SEQUENCE: 12

```
atgctaaaat acaaaccttt actaaaaatc tcgaagaact gtgaggctgc tatcctcaga     60
gcgtctaaga ctagattgaa cacaatccgc gcgtacggtt ctaccgttcc aaaatccaag    120
tcgttcgaac aagactcaag aaaacgcaca cagtcatgga ctgccttgag agtcggtgca    180
attctagccg ctactagttc cgtggcgtat ctaaactggc ataatggcca aatagacaac    240
gagccgaaac tggatatgaa taaacaaaag atttcgcccg ctgaagttgc caagcataac    300
aagcccgatg attgttgggt tgtgatcaat ggttacgtat acgacttaac gcgattccta    360
ccaaatcatc caggtgggca ggatgttatc aagtttaacg ccgggaaaga tgtcactgct    420
atttttgaac cactacatgc tcctaatgtc atcgataagt atatagctcc cgagaaaaaa    480
ttgggtcccc ttcaaggatc catgcctcct gaacttgtct gtcctcctta tgctcctggt    540
gaaactaagg aagatatcgc tagaaaagaa caactaaaat cgctgctacc tcctctagat    600
aatattatta acctttacga ctttgaatac ttggcctctc aaactttgac taaacaagcg    660
tgggcctact attcctccgg tgctaacgac gaagttactc acagagaaaa ccataatgct    720
tatcatagga tttttttcaa accaaagatc cttgtagatg tacgcaaagt agacatttca    780
actgacatgt tgggttctca tgtggatgtt cccttctacg tgtctgctac agctttgtgt    840
aaactgggaa accccttaga aggtgaaaaa gatgtcgcca gaggttgtgg ccaaggtgtg    900
acaaaagtcc cacaaatgat atctactttg gcttcatgtt cccctgagga aattattgaa    960
gcagcaccct ctgataaaca aattcaatgg taccaactat atgttaactc tgatagaaag   1020
atcactgatg atttggttaa aaatgtagaa aagctgggtg taaaggcatt atttgtcact   1080
gtggatgctc caagtttagg tcaaagagaa aaagatatga agctgaaatt ttccaataca   1140
aaggctggtc caaaagcgat gaagaaaact aatgtagaag aatctcaagg tgcttcgaga   1200
gcgttatcaa agtttattga cccctctttg acttggaaag atatagaaga gttgaagaaa   1260
aagacaaaac tacctattgt tatcaaaggt gttcaacgta ccgaagatgt tatcaaagca   1320
gcagaaatcg gtgtaagtgg ggtggttcta tccaatcatg gtggtagaca attagatttt   1380
tcaagggctc ccattgaagt cctggctgaa accatgccaa tcctggaaca acgtaacttg   1440
aaggataagt tggaagtttt cgtggacggt ggtgttcgtc gtggtacaga tgtcttgaaa   1500
```

gcgttatgtc taggtgctaa aggtgttggt ttgggtagac cattcttgta tgcgaactca 1560
tgctatggtc gtaatggtgt tgaaaaagcc attgaaattt taagagatga aattgaaatg 1620
tctatgagac tattaggtgt tactagcatt gcggaattga agcctgatct tttagatcta 1680
tcaacactaa aggcaagaac agttggagta ccaaacgacg tgctgtataa tgaagtttat 1740
gagggaccta ctttaacaga atttgaggat gcatga 1776

<210> SEQ ID NO 13
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 13
ttcgcggcca cctacgccgc tatctttgca acaactatct gcgataactc agcaaatttt 60
gcatattcgt gttgcagtat tgcgataatg ggagtcttac ttccaacata acggcagaaa 120
gaaatgtgag aaaattttgc atcctttgcc tccgttcaag tatataaagt cggcatgctt 180
gataatcttt ctttccatcc tacattgttc taattattct tattctcctt tattctttcc 240
taacatacca agaaattaat cttctgtcat tcgcttaaac actatatcaa ta 292

<210> SEQ ID NO 14
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 14
atttggcgag cgttggttgg tggatcaagc ccacgcgtag gcaatcctcg agcagatccg 60
ccaggcgtgt atatatagcg tggatggcca ggcaacttta gtgctgacac atacaggcat 120
atatatatgt gtgcgacgac acatgatcat atggcatgca tgtgctctgt atgtatataa 180
aactcttgtt ttcttctttt ctctaaatat tctttcctta tacattagga cctttgcagc 240
ataaattact atacttctat agacacgcaa acacaaatac acacactaa 289

<210> SEQ ID NO 15
<211> LENGTH: 401
<212> TYPE: DNA
<213> ORGANISM: Artificial Sequence
<220> FEATURE:
<223> OTHER INFORMATION: Synthetic TEF1 promoter

<400> SEQUENCE: 15
atagcttcaa aatgtttcta ctcctttttt actcttccag attttctcgg actccgcgca 60
tcgccgtacc acttcaaaac acccaagcac agcatactaa atttcccctc tttcttcctc 120
tagggtgtcg ttaattaccc gtactaaagg tttggaaaag aaaaaagaga ccgcctcgtt 180
tctttttctt cgtcgaaaaa ggcaataaaa atttttatca cgtttctttt tcttgaaaat 240
tttttttttg atttttttct ctttcgatga cctcccattg atatttaagt taataaacgg 300
tcttcaattt ctcaagtttc agtttcattt ttcttgttct attacaactt tttttacttc 360
ttgctcatta gaaagaaagc atagcaatct aatctaagtt t 401

<210> SEQ ID NO 16
<211> LENGTH: 798
<212> TYPE: DNA

<213> ORGANISM: Artificial Sequence
<220> FEATURE:
<223> OTHER INFORMATION: Synthetic PGK1 promoter

<400> SEQUENCE: 16

```
ctttcctctt tttattaacc ttaattttta ttttagattc ctgacttcaa ctcaagacgc     60

acagatatta taacatctgc ataataggca tttgcaagaa ttactcgtga gtaaggaaag    120

agtgaggaac tatcgcatac ctgcatttaa agatgccgat ttgggcgcga atcctttatt    180

ttggcttcac cctcatacta ttatcagggc cagaaaaagg aagtgtttcc ctccttcttg    240

aattgatgtt accctcataa agcacgtggc ctcttatcga gaaagaaatt accgtcgctc    300

gtgatttgtt tgcaaaaaga acaaaactga aaaaacccag acacgctcga cttcctgtct    360

tcctattgat tgcagcttcc aatttcgtca cacaacaagg tcctagcgac ggctcacagg    420

ttttgtaaca agcaatcgaa ggttctggaa tggcgggaaa gggtttagta ccacatgcta    480

tgatgcccac tgtgatctcc agagcaaagt tcgttcgatc gtactgttac tctctctctt    540

tcaaacagaa ttgtccgaat cgtgtgacaa caacagcctg ttctcacaca ctcttttctt    600

ctaaccaagg gggtggttta gtttagtaga acctcgtgaa acttacattt acatatatat    660

aaacttgcat aaattggtca atgcaagaaa tacatatttg gtcttttcta attcgtagtt    720

tttcaagttc ttagatgctt tctttttctc ttttttacag atcatcaagg aagtaattat    780

ctacttttta caacaaat                                                  798
```

<210> SEQ ID NO 17
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 17

```
agtttatcat tatcaatact cgccatttca aagaatacgt aaataattaa tagtagtgat     60

tttcctaact ttatttagtc aaaaaattag ccttttaatt ctgctgtaac ccgtacatgc    120

ccaaaatagg gggcgggtta cacagaatat ataacatcgt aggtgtctgg gtgaacagtt    180

tattcctggc atccactaaa tataatggag cccgcttttt aagctggcat ccagaaaaaa    240

aaagaatccc agcaccaaaa tattgttttc ttcaccaacc atcagttcat aggtccattc    300

tcttagcgca actacagaga acaggggcac aaacaggcaa aaaacgggca caacctcaat    360

ggagtgatgc aacctgcctg gagtaaatga tgacacaagg caattgaccc acgcatgtat    420

ctatctcatt ttcttacacc ttctattacc ttctgctctc tctgatttgg aaaaagctga    480

aaaaaaaggt tgaaaccagt tccctgaaat tattccccta cttgactaat aagtatataa    540

agacggtagg tattgattgt aattctgtaa atctatttct taaacttctt aaattctact    600

tttatagtta gtcttttttt tagttttaaa acaccagaac ttagtttcga cggat         655
```

<210> SEQ ID NO 18
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 18

```
gccgggatcg aagaaatgat ggtaaatgaa ataggaaatc aaggagcatg aaggcaaaag     60

acaaatataa gggtcgaacg aaaaataaag tgaaaagtgt tgatatgatg tatttggctt    120
```

```
tgcggcgccg aaaaaacgag tttacgcaat tgcacaatca tgctgactct gtggcggacc    180

cgcgctcttg ccggcccggc gataacgctg ggcgtgaggc tgtgcccggc ggagtttttt    240

gcgcctgcat tttccaaggt ttaccctgcg ctaaggggcg agattggaga agcaataaga    300

atgccggttg gggttgcgat gatgacgacc acgacaactg gtgtcattat ttaagttgcc    360

gaaagaacct gagtgcattt gcaacatgag tatactagaa gaatgagcca agacttgcga    420

gacgcgagtt tgccggtggt gcgaacaata gagcgaccat gaccttgaag gtgagacgcg    480

cataaccgct agagtacttt gaagaggaaa cagcaatagg gttgctacca gtataaatag    540

acaggtacat acaacactgg aaatggttgt ctgtttgagt acgctttcaa ttcatttggg    600

tgtgcacttt attatgttac aatatggaag ggaactttac acttctccta tgcacatata    660

ttaattaaag tccaatgcta gtagagaagg ggggtaacac ccctccgcgc tcttttccga    720

tttttttcta aaccgtggaa tatttcggat atccttttgt tgtttccggg tgtacaatat    780

ggacttcctc ttttctggca accaaaccca tacatcggga ttcctataat accttcgttg    840

gtctccctaa catgtaggtg gcggagggga gatatacaat agaacagata ccagacaaga    900

cataatgggc taaacaagac tacaccaatt acactgcctc attgatggtg gtacataacg    960

aactaatact gtagccctag acttgatagc catcatcata tcgaagtttc actacccttt   1020

ttccatttgc catctattga agtaataata ggcgcatgca acttcttttc ttttttttc   1080

ttttctctct cccccgttgt tgtctcacca tatccgcaat gacaaaaaaa tgatggaaga   1140

cactaaagga aaaaattaac gacaaagaca gcaccaacag atgtcgttgt tccagagctg   1200

atgaggggta tctcgaagca cacgaaactt tttccttcct tcattcacgc acactactct   1260

ctaatgagca acggtatacg gccttccttc cagttacttg aatttgaaat aaaaaaaagt   1320

ttgctgtctt gctatcaagt ataaatagac ctgcaattat taatcttttg tttcctcgtc   1380

attgttctcg ttccctttct tccttgtttc tttttctgca caatatttca agctatacca   1440

agcatacaat caactccaag ctggccgc                                      1468
```

<210> SEQ ID NO 19
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 19

```
tcatgtaatt agttatgtca cgcttacatt cacgccctcc ccccacatcc gctctaaccg     60

aaaaggaagg agttagacaa cctgaagtct aggtccctat ttattttttt atagttatgt    120

tagtattaag aacgttattt atatttcaaa tttttctttt ttttctgtac agacgcgtgt    180

acgcatgtaa cattatactg aaaaccttgc ttgagaaggt tttgggacgc tcgaaggctt    240

taatttgcgg cc                                                        252
```

<210> SEQ ID NO 20
<211> LENGTH: 31
<212> TYPE: DNA
<213> ORGANISM: Artificial Sequence
<220> FEATURE:
<223> OTHER INFORMATION: Synthetic forward primer

<400> SEQUENCE: 20

```
cgagctcttc gcggccacct acgccgctat c                                    31
```

<210> SEQ ID NO 21
<211> LENGTH: 32
<212> TYPE: DNA
<213> ORGANISM: Artificial Sequence
<220> FEATURE:
<223> OTHER INFORMATION: Synthetic reverse primer

<400> SEQUENCE: 21
gctctagata ttgatatagt gtttaagcga at 32

<210> SEQ ID NO 22
<211> LENGTH: 34
<212> TYPE: DNA
<213> ORGANISM: Artificial Sequence
<220> FEATURE:
<223> OTHER INFORMATION: Synthetic primer

<400> SEQUENCE: 22
aattgaattc atggcaacat taaaagatca acta 34

<210> SEQ ID NO 23
<211> LENGTH: 35
<212> TYPE: DNA
<213> ORGANISM: Artificial Sequence
<220> FEATURE:
<223> OTHER INFORMATION: Synthetic primer

<400> SEQUENCE: 23
aattgtcgac ttagaattgt aattcctttt ggatg 35

<210> SEQ ID NO 24
<211> LENGTH: 40
<212> TYPE: DNA
<213> ORGANISM: Artificial Sequence
<220> FEATURE:
<223> OTHER INFORMATION: Synthetic primer

<400> SEQUENCE: 24
gcggccgcga attcggatcc gtagatacat tgatgctatc 40

<210> SEQ ID NO 25
<211> LENGTH: 29
<212> TYPE: DNA
<213> ORGANISM: Artificial Sequence
<220> FEATURE:
<223> OTHER INFORMATION: Synthetic primer

<400> SEQUENCE: 25
gcggccgctc cgcggctcgt gctatattc 29

<210> SEQ ID NO 26
<211> LENGTH: 23
<212> TYPE: DNA
<213> ORGANISM: Artificial Sequence
<220> FEATURE:
<223> OTHER INFORMATION: Synthetic primer

<400> SEQUENCE: 26
gaattcaaca agctcatgca aag 23

<210> SEQ ID NO 27
<211> LENGTH: 27
<212> TYPE: DNA
<213> ORGANISM: Artificial Sequence
<220> FEATURE:
<223> OTHER INFORMATION: Synthetic primer

<400> SEQUENCE: 27
gaattcctcg aggatttgac tgtgtta 27

<210> SEQ ID NO 28
<211> LENGTH: 26
<212> TYPE: DNA
<213> ORGANISM: Artificial Sequence
<220> FEATURE:
<223> OTHER INFORMATION: Synthetic primer

<400> SEQUENCE: 28
ccgctcgaga tgattgaaca agatgg 26

<210> SEQ ID NO 29
<211> LENGTH: 27
<212> TYPE: DNA
<213> ORGANISM: Artificial Sequence
<220> FEATURE:
<223> OTHER INFORMATION: Synthetic primer

<400> SEQUENCE: 29
cgcggatcct cagaagaact cgtcaag 27

<210> SEQ ID NO 30
<211> LENGTH: 60
<212> TYPE: DNA
<213> ORGANISM: Artificial Sequence
<220> FEATURE:
<223> OTHER INFORMATION: Synthetic primer

<400> SEQUENCE: 30
aagatctacg aagttgaagg tatgagatgg gctggtaacg taatacgact cactataggg 60

<210> SEQ ID NO 31
<211> LENGTH: 61
<212> TYPE: DNA
<213> ORGANISM: Artificial Sequence
<220> FEATURE:
<223> OTHER INFORMATION: Synthetic primer

<400> SEQUENCE: 31
gcttccttaa cttctggctt ggacaaggta ccgacgtaaa aacaagctca tgcaaagagg 60
t 61

<210> SEQ ID NO 32
<211> LENGTH: 22
<212> TYPE: DNA
<213> ORGANISM: Artificial Sequence
<220> FEATURE:
<223> OTHER INFORMATION: Synthetic primer

<400> SEQUENCE: 32
gctcttctct accctgtcat tc 22

<210> SEQ ID NO 33
<211> LENGTH: 22
<212> TYPE: DNA
<213> ORGANISM: Artificial Sequence
<220> FEATURE:
<223> OTHER INFORMATION: Synthetic primer

<400> SEQUENCE: 33
tagtgtacag ggtgtcgtat ct 22

<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34
tctctataat gaagaccctt gtgc 24

<210> SEQ ID NO 35
<211> LENGTH: 57
<212> TYPE: DNA
<213> ORGANISM: Artificial Sequence
<220> FEATURE:
<223> OTHER INFORMATION: Synthetic primer

<400> SEQUENCE: 35
ccaattcgcc ctatagtgag tcgtattact atgcgggaac tgtattagcg acatagg 57

<210> SEQ ID NO 36
<211> LENGTH: 60
<212> TYPE: DNA
<213> ORGANISM: Artificial Sequence
<220> FEATURE:
<223> OTHER INFORMATION: Synthetic primer

<400> SEQUENCE: 36
agcttttgtt ccctttagtg agggttaatt cgacgtgctg tataatgaag tttatgaggg 60

<210> SEQ ID NO 37
<211> LENGTH: 22
<212> TYPE: DNA
<213> ORGANISM: Artificial Sequence
<220> FEATURE:
<223> OTHER INFORMATION: Synthetic primer

<400> SEQUENCE: 37
gtggatattt acagaacgat gc 22

<210> SEQ ID NO 38
<211> LENGTH: 5457
<212> TYPE: DNA
<213> ORGANISM: Artificial Sequence
<220> FEATURE:
<223> OTHER INFORMATION: Synthetic pCtB1 vector

<400> SEQUENCE: 38
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtacgcatt taagcataaa cacgcactat gccgttcttc tcatgtatat 180
atatatacag gcaacacgca gatataggtg cgacgtgaac agtgagctgt atgtgcgcag 240
ctcgcgttgc attttcggaa gcgctcgttt tcggaaacgc tttgaagttc ctattccgaa 300
gttcctattc tctagctaga aagtatagga acttcagagc gcttttgaaa accaaaagcg 360
ctctgaagac gcactttcaa aaaaccaaaa acgcaccgga ctgtaacgag ctactaaaat 420
attgcgaata ccgcttccac aaacattgct caaaagtatc tctttgctat atatctctgt 480
gctatatccc tatataacct acccatccac ctttcgctcc ttgaacttgc atctaaactc 540
gacctctaca ttttttatgt ttatctctag tattactctt tagacaaaaa aattgtagta 600
agaactattc atagagtgaa tcgaaaacaa tacgaaaatg taaacatttc ctatacgtag 660

```
tatatagaga caaaatagaa gaaaccgttc ataattttct gaccaatgaa gaatcatcaa    720
cgctatcact ttctgttcac aaagtatgcg caatccacat cggtatagaa tataatcggg    780
gatgccttta tcttgaaaaa atgcacccgc agcttcgcta gtaatcagta aacgcgggaa    840
gtggagtcag gcttttttta tggaagagaa aatagacacc aaagtagcct tcttctaacc    900
ttaacggacc tacagtgcaa aaagttatca agagactgca ttatagagcg cacaaaggag    960
aaaaaaagta atctaagatg ctttgttaga aaaatagcgc tctcgggatg catttttgta   1020
gaacaaaaaa gaagtataga ttctttgttg gtaaaatagc gctctcgcgt tgcatttctg   1080
ttctgtaaaa atgcagctca gattctttgt ttgaaaaatt agcgctctcg cgttgcattt   1140
ttgttttaca aaaatgaagc acagattctt cgttggtaaa atagcgcttt cgcgttgcat   1200
ttctgttctg taaaaatgca gctcagattc tttgtttgaa aaattagcgc tctcgcgttg   1260
catttttgtt ctacaaaatg aagcacagat gcttcgttaa tgtgctgcaa ggcgattaag   1320
ttgggtaacg ccagggtttt cccagtcacg acgttgtaaa acgacggcca gtgaattgta   1380
atacgactca ctatagggcg aattgggtac cgggcccccc ctcgaggtcg acggtatcga   1440
taagcttgat atcgaattcc tgcagcccgg gggatccact agttctagag cggccgccac   1500
cgcggtggag ctcggttctg cttatcctta cgacgtgcct gactacgcct gaacccgatg   1560
caaatgagac gatcgtctat tcctggtccg gttttctctg ccctctcttc tattcacttt   1620
ttttatactt tatataaaat tatataaatg acataactga aacgccacac gtcctctcct   1680
attcgttaac gcctgtctgt agcgctgtta ctgaagctgc gcaagtagtt ttttcaccgt   1740
ataggccctc tttttctctc tctttctttc tctcccgcgc tgatctcttc ttcgaaacac   1800
agagtgcacc ataccacctt ttcaattcat catttttttt ttattctttt ttttgatttc   1860
ggtttccttg aaattttttt gattcggtaa tctccgaaca gaaggaagaa cgaaggaagg   1920
agcacagact tagattggta tatatacgca tatgtagtgt tgaagaaaca tgaaattgcc   1980
cagtattctt aacccaactg cacagaacaa aaacctccag gaaacgaaga taaatcatgt   2040
cgaaagctac atataaggaa cgtgctgcta ctcatcctag tcctgttgct gccaagctat   2100
ttaatatcat gcacgaaaag caaacaaact tgtgtgcttc attggatgtt cgtaccacca   2160
aggaattact ggagttagtt gaagcattag gtcccaaaat ttgtttacta aaaacacatg   2220
tggatatctt gactgatttt tccatggagg gcacagttaa gccgctaaag gcattatccg   2280
ccaagtacaa tttttactc ttcgaagaca gaaaatttgc tgacattggt aatacagtca   2340
aattgcagta ctctgcgggt gtatacagaa tagcagaatg ggcagacatt acgaatgcac   2400
acggtgtggt gggcccaggt attgttagcg gtttgaagca ggcggcagaa gaagtaacaa   2460
aggaacctag aggccttttg atgttagcag aattgtcatg caagggctcc ctatctactg   2520
gagaatatac taagggtact gttgacattg cgaagagcga caaagatttt gttatcggct   2580
ttattgctca aagagacatg ggtggaagag atgaaggtta cgattggttg attatgacac   2640
ccggtgtggg tttagatgac aagggagacg cattgggtca acagtataga accgtggatg   2700
atgtggtctc tacaggatct gacattatta ttgttggaag aggactattt gcaaagggaa   2760
gggatgctaa ggtagagggt gaacgttaca gaaaagcagg ctgggaagca tatttgagaa   2820
gatgcggcca gcaaaactaa tcatgtaatt agttatgtca cgcttacatt cacgccctcc   2880
ccccacatcc gctctaaccg aaaaggaagg agttagacaa cctgaagtct aggtccctat   2940
ttattttttt atagttatgt tagtattaag aacgttattt atatttcaaa tttttctttt   3000
```

-continued

```
ttttctgtac agacgcgtgt acgcatgtaa cattatactg aaaaccttgc ttgagaaggt   3060
tttgggacgc tcgaaggctt taatttgcgt ctgtagcgct gttactgaag ctgcgcaagt   3120
agttttttca ccgtataggc cctctttttc tctctctttc tttctctccc gcgctgatct   3180
cttcttcgaa acatcatgaa taaaaagaaa aaggaaatca agaaaaaaaa gccataattt   3240
atcccacatt ttttttatt gtcgctgttc acaccgcata acgaagatat tggctagcta   3300
accagctttt gttcccttta gtgagggtta atttcgagct tggcgtaatc atggtcatag   3360
ctgtttcctg tgtgaaattg ttatccgctc acaattccac acaacatacg agccggaagc   3420
ataaagtgta aagcctgggg tgcctaatga gtgagctaac tcacattaat tgcgttgcgc   3480
tcactgcccg ctttccagtc gggaaacctg tcgtgccagc tgcattaatg aatcggccaa   3540
cgcgcgggga gaggcggttt gcgtattggg cgctcttccg cttcctcgct cactgactcg   3600
ctgcgctcgg tcgttcggct gcggcgagcg gtatcagctc actcaaaggc ggtaatacgg   3660
ttatccacag aatcagggga taacgcagga aagaacatgt gagcaaaagg ccagcaaaag   3720
gccaggaacc gtaaaaaggc cgcgttgctg gcgtttttcc ataggctccg cccccctgac   3780
gagcatcaca aaaatcgacg ctcaagtcag aggtggcgaa acccgacagg actataaaga   3840
taccaggcgt ttccccctgg aagctccctc gtgcgctctc ctgttccgac cctgccgctt   3900
accggatacc tgtccgcctt tctcccttcg ggaagcgtgg cgctttctca tagctcacgc   3960
tgtaggtatc tcagttcggt gtaggtcgtt cgctccaagc tgggctgtgt gcacgaaccc   4020
cccgttcagc ccgaccgctg cgccttatcc ggtaactatc gtcttgagtc caacccggta   4080
agacacgact tatcgccact ggcagcagcc actggtaaca ggattagcag agcgaggtat   4140
gtaggcggtg ctacagagtt cttgaagtgg tggcctaact acggctacac tagaaggaca   4200
gtatttggta tctgcgctct gctgaagcca gttaccttcg gaaaaagagt tggtagctct   4260
tgatccggca aacaaaccac cgctggtagc ggtggttttt ttgtttgcaa gcagcagatt   4320
acgcgcagaa aaaaaggatc tcaagaagat cctttgatct tttctacggg gtctgacgct   4380
cagtggaacg aaaactcacg ttaagggatt ttggtcatga gattatcaaa aaggatcttc   4440
acctagatcc ttttaaatta aaaatgaagt tttaaatcaa tctaaagtat atatgagtaa   4500
acttggtctg acatcagaag aactcgtcaa gaaggcgata gaaggcgatg cgctgcgaat   4560
cgggagcggc gataccgtaa agcacgagga agcggtcagc ccattcgccg ccaagctctt   4620
cagcaatatc acgggtagcc aacgctatgt cctgatagcg gtccgccaca cccagccggc   4680
cacagtcgat gaatccagaa aagcggccat tttccaccat gatattcggc aagcaggcat   4740
cgccatgggt cacgacgaga tcctcgccgt cgggcatgct cgccttgagc ctggcgaaca   4800
gttcggctgg cgcgagcccc tgatgctctt cgtccagatc atcctgatcg acaagaccgg   4860
cttccatccg agtacgtgct cgctcgatgc gatgtttcgc ttggtggtcg aatgggcagg   4920
tagccggatc aagcgtatgc agccgccgca ttgcatcagc catgatggat actttctcgg   4980
caggagcaag gtgagatgac aggagatcct gccccggcac ttcgcccaat agcagccagt   5040
cccttcccgc ttcagtgaca acgtcgagca cagctgcgca aggaacgccc gtcgtggcca   5100
gccacgatag ccgcgctgcc tcgtcttgca gttcattcag ggcaccggac aggtcggtct   5160
tgacaaaaag aaccgggcgc ccctgcgctg acagccggaa cacggcggca tcagagcagc   5220
cgattgtctg ttgtgcccag tcatagccga atagcctctc cacccaagcg gccggagaac   5280
ctgcgtgcaa tccatcttgt tcaattcgag tgcattcaac atcagccata ctcttccttt   5340
ttcaatatta ttgaagcatt tatcagggtt attgtctcat gagcggatac atatttgaat   5400
```

gtatttagaa aaataaacaa ataggggttc cgcgcacatt tccccgaaaa gtgccac 5457

<210> SEQ ID NO 39
<211> LENGTH: 21
<212> TYPE: DNA
<213> ORGANISM: Artificial Sequence
<220> FEATURE:
<223> OTHER INFORMATION: Synthetic primer

<400> SEQUENCE: 39
gcacaacacg agatctttca c 21

<210> SEQ ID NO 40
<211> LENGTH: 23
<212> TYPE: DNA
<213> ORGANISM: Artificial Sequence
<220> FEATURE:
<223> OTHER INFORMATION: Synthetic primer

<400> SEQUENCE: 40
aaagagaaga ggtacaaagg agg 23

<210> SEQ ID NO 41
<211> LENGTH: 44
<212> TYPE: DNA
<213> ORGANISM: Artificial Sequence
<220> FEATURE:
<223> OTHER INFORMATION: Synthetic primer

<400> SEQUENCE: 41
ctatagggcg aattggactg taccgaatat ctgtgtccta atga 44

<210> SEQ ID NO 42
<211> LENGTH: 53
<212> TYPE: DNA
<213> ORGANISM: Artificial Sequence
<220> FEATURE:
<223> OTHER INFORMATION: Synthetic primer

<400> SEQUENCE: 42
ctcgaggggg ggcccggtac ctattgatat agtgtttaag cgaatgacag aag 53

<210> SEQ ID NO 43
<211> LENGTH: 7026
<212> TYPE: DNA
<213> ORGANISM: Artificial Sequence
<220> FEATURE:
<223> OTHER INFORMATION: Synthetic MD0922 vector

<400> SEQUENCE: 43
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtacgcatt taagcataaa cacgcactat gccgttcttc tcatgtatat 180
atatatacag gcaacacgca gatataggtg cgacgtgaac agtgagctgt atgtgcgcag 240
ctcgcgttgc attttcggaa gcgctcgttt tcggaaacgc tttgaagttc ctattccgaa 300
gttcctattc tctagctaga aagtatagga acttcagagc gcttttgaaa accaaaagcg 360
ctctgaagac gcactttcaa aaaaccaaaa acgcaccgga ctgtaacgag ctactaaaat 420
attgcgaata ccgcttccac aaacattgct caaaagtatc tctttgctat atatctctgt 480
gctatatccc tatataacct acccatccac ctttcgctcc ttgaacttgc atctaaactc 540

-continued

```
gacctctaca tttttatgt ttatctctag tattactctt tagacaaaaa aattgtagta    600
agaactattc atagagtgaa tcgaaaacaa tacgaaaatg taaacatttc ctatacgtag    660
tatatagaga caaaatagaa gaaaccgttc ataattttct gaccaatgaa gaatcatcaa    720
cgctatcact ttctgttcac aaagtatgcg caatccacat cggtatagaa tataatcggg    780
gatgccttta tcttgaaaaa atgcacccgc agcttcgcta gtaatcagta aacgcgggaa    840
gtggagtcag gcttttttta tggaagagaa aatagacacc aaagtagcct tcttctaacc    900
ttaacggacc tacagtgcaa aaagttatca agagactgca ttatagagcg cacaaaggag    960
aaaaaaagta atctaagatg ctttgttaga aaaatagcgc tctcgggatg catttttgta   1020
gaacaaaaaa gaagtataga ttctttgttg gtaaaatagc gctctcgcgt tgcatttctg   1080
ttctgtaaaa atgcagctca gattctttgt ttgaaaaatt agcgctctcg cgttgcattt   1140
ttgttttaca aaaatgaagc acagattctt cgttggtaaa atagcgcttt cgcgttgcat   1200
ttctgttctg taaaaatgca gctcagattc tttgtttgaa aaattagcgc tctcgcgttg   1260
catttttgtt ctacaaaatg aagcacagat gcttcgttaa tgtgctgcaa ggcgattaag   1320
ttgggtaacg ccagggtttt cccagtcacg acgttgtaaa acgacggcca gtgaattgta   1380
atacgactca ctatagggcg aattggactg taccgaatat ctgtgtccta atgaattcct   1440
cgttagtggt cattattata tacgatagtt gtagttttcc ctgttttccc tttgttcctt   1500
tttttcgagt ctagtattta ccaatataga agaaagagaa aataaaataag gtttcttgtt   1560
agagattagt tacttttgct attattatcg caaattcctc ttccactata caaacaagaa   1620
agtaattact actcttattg taagatagta tgataatttc gacgatagat aatatttgct   1680
tttcgttggc cttttctttt ttttttcct tccttccctt cgaagatcct cccgtataat   1740
aacgccgcca gaccatgtag ggtaaccaga gaatacgccc actccgcttt cgcatgtggc   1800
actcctgtat gtcaaaatgc cgaataatct ccatccatga cgaagcgctt tgaggtgttt   1860
aattatatac agggcaaagt cttggagata aagaacgctt tcctaacaac ttgcgctatt   1920
cctcttattt ccttcaatcg attaaaatta actttaatc gacattgtct tttaaaccag   1980
ggcaaagcaa aataaaagaa acttaatacg ttatgccgta atgaagggct accaaaaacg   2040
ataatctcaa ctgtaaacag gtacaatgcg gacccttttg ccacaaaaca tacatcattc   2100
attgccggaa aaagaaagaa gtgaagacag cagtgcagcc agccatgttg cgccaatcta   2160
attatagatg ctggtgccct gaggatgtat ctggagccag ccatggcatc atgcgctacc   2220
gccggatgta aaatccgaca cgcaaaagaa aaccttcgag gttgcgcact tcgcccaccc   2280
atgaaccaca cggttagtcc aaaaggggca gttcagattc cagatgcggg aattagcttg   2340
ctgccaccct cacctcacta acgctgcggt gtgcggatac ttcatgctat ttatagacgc   2400
gcgtgtcgga atcagcacgc gcaagaacca aatgggaaaa tcggaatggg tccagaactg   2460
ctttgagtgc tggctattgg cgtctgattt ccgttttggg aatcctttgc cgcgcgcccc   2520
tctcaaaact ccgcacaagt cccagaaagc gggaaagaaa taaaacgcca ccaaaaaaaa   2580
aaaaataaaa gccaatcctc gaagcgtggg tggtaggccc tggattatcc cgtacaagta   2640
tttctcagga gtaaaaaaac cgtttgtttt ggaattcccc atttcgcggc cacctacgcc   2700
gctatctttg caacaactat ctgcgataac tcagcaaatt ttgcatattc gtgttgcagt   2760
attgcgataa tgggagtctt acttccaaca taacggcaga aagaaatgtg agaaaatttt   2820
gcatcctttg cctccgttca agtatataaa gtcggcatgc ttgataatct ttctttccat   2880
cctacattgt tctaattatt cttattctcc tttattcttt cctaacatac caagaaatta   2940
```

atcttctgtc attcgcttaa acactatatc aataggtacc gggccccccc tcgaggtcga 3000
cggtatcgat aagcttgata tcgaattcct gcagcccggg ggatccacta gttctagagc 3060
ggccgccacc gcggtggagc tcggttctgc ttatccttac gacgtgcctg actacgcctg 3120
aacccgatgc aaatgagacg atcgtctatt cctggtccgg ttttctctgc cctctcttct 3180
attcactttt tttatacttt atataaaatt atataaatga cataactgaa acgccacacg 3240
tcctctccta ttcgttaacg cctgtctgta gcgctgttac tgaagctgcg caagtagttt 3300
tttcaccgta taggccctct ttttctctct ctttctttct ctcccgcgct gatctcttct 3360
tcgaaacaca gagtgcacca taccaccttt tcaattcatc attttttttt tattcttttt 3420
tttgatttcg gtttccttga aattttttttg attcggtaat ctccgaacag aaggaagaac 3480
gaaggaagga gcacagactt agattggtat atatacgcat atgtagtgtt gaagaaacat 3540
gaaattgccc agtattctta acccaactgc acagaacaaa aacctccagg aaacgaagat 3600
aaatcatgtc gaaagctaca tataaggaac gtgctgctac tcatcctagt cctgttgctg 3660
ccaagctatt taatatcatg cacgaaaagc aaacaaactt gtgtgcttca ttggatgttc 3720
gtaccaccaa ggaattactg gagttagttg aagcattagg tcccaaaatt tgtttactaa 3780
aaacacatgt ggatatcttg actgattttt ccatggaggg cacagttaag ccgctaaagg 3840
cattatccgc caagtacaat tttttactct tcgaagacag aaaatttgct gacattggta 3900
atacagtcaa attgcagtac tctgcgggtg tatacagaat agcagaatgg gcagacatta 3960
cgaatgcaca cggtgtggtg ggcccaggta ttgttagcgg tttgaagcag gcggcagaag 4020
aagtaacaaa ggaacctaga ggccttttga tgttagcaga attgtcatgc aagggctccc 4080
tatctactgg agaatatact aagggtactg ttgacattgc gaagagcgac aaagattttg 4140
ttatcggctt tattgctcaa agagacatgg gtggaagaga tgaaggttac gattggttga 4200
ttatgacacc cggtgtgggt ttagatgaca agggagacgc attgggtcaa cagtatagaa 4260
ccgtggatga tgtggtctct acaggatctg acattattat tgttggaaga ggactatttg 4320
caaagggaag ggatgctaag gtagagggtg aacgttacag aaaagcaggc tgggaagcat 4380
atttgagaag atgcggccag caaaactaat catgtaatta gttatgtcac gcttacattc 4440
acgccctccc cccacatccg ctctaaccga aaaggaagga gttagacaac ctgaagtcta 4500
ggtccctatt tattttttta tagttatgtt agtattaaga acgttattta tatttcaaat 4560
ttttcttttt tttctgtaca gacgcgtgta cgcatgtaac attatactga aaaccttgct 4620
tgagaaggtt ttgggacgct cgaaggcttt aatttgcgtc tgtagcgctg ttactgaagc 4680
tgcgcaagta gtttttttcac cgtataggcc ctctttttct ctctctttct ttctctcccg 4740
cgctgatctc ttcttcgaaa catcatgaat aaaaagaaaa aggaaatcaa gaaaaaaaag 4800
ccataattta tcccacattt ttttttattg tcgctgttca caccgcataa cgaagatatt 4860
ggctagctaa ccagcttttg ttccctttag tgagggttaa tttcgagctt ggcgtaatca 4920
tggtcatagc tgtttcctgt gtgaaattgt tatccgctca caattccaca caacatacga 4980
gccggaagca taaagtgtaa agcctggggt gcctaatgag tgagctaact cacattaatt 5040
gcgttgcgct cactgcccgc tttccagtcg ggaaacctgt cgtgccagct gcattaatga 5100
atcggccaac gcgcggggag aggcggtttg cgtattgggc gctcttccgc ttcctcgctc 5160
actgactcgc tgcgctcggt cgttcggctg cggcgagcgg tatcagctca ctcaaaggcg 5220
gtaatacggt tatccacaga atcaggggat aacgcaggaa agaacatgtg agcaaaaggc 5280

-continued cagcaaaagg ccaggaaccg taaaaaggcc gcgttgctgg cgtttttcca taggctccgc 5340
ccccctgacg agcatcacaa aaatcgacgc tcaagtcaga ggtggcgaaa cccgacagga 5400
ctataaagat accaggcgtt tccccctgga agctccctcg tgcgctctcc tgttccgacc 5460
ctgccgctta ccggatacct gtccgccttt ctcccttcgg gaagcgtggc gctttctcat 5520
agctcacgct gtaggtatct cagttcggtg taggtcgttc gctccaagct gggctgtgtg 5580
cacgaacccc ccgttcagcc cgaccgctgc gccttatccg gtaactatcg tcttgagtcc 5640
aacccggtaa gacacgactt atcgccactg gcagcagcca ctggtaacag gattagcaga 5700
gcgaggtatg taggcggtgc tacagagttc ttgaagtggt ggcctaacta cggctacact 5760
agaaggacag tatttggtat ctgcgctctg ctgaagccag ttaccttcgg aaaaagagtt 5820
ggtagctctt gatccggcaa acaaaccacc gctggtagcg gtggtttttt tgtttgcaag 5880
cagcagatta cgcgcagaaa aaaaggatct caagaagatc ctttgatctt ttctacgggg 5940
tctgacgctc agtggaacga aaactcacgt taagggattt tggtcatgag attatcaaaa 6000
aggatcttca cctagatcct tttaaattaa aaatgaagtt ttaaatcaat ctaaagtata 6060
tatgagtaaa cttggtctga catcagaaga actcgtcaag aaggcgatag aaggcgatgc 6120
gctgcgaatc gggagcggcg ataccgtaaa gcacgaggaa gcggtcagcc cattcgccgc 6180
caagctcttc agcaatatca cgggtagcca acgctatgtc ctgatagcgg tccgccacac 6240
ccagccggcc acagtcgatg aatccagaaa agcggccatt ttccaccatg atattcggca 6300
agcaggcatc gccatgggtc acgacgagat cctcgccgtc gggcatgctc gccttgagcc 6360
tggcgaacag ttcggctggc gcgagcccct gatgctcttc gtccagatca tcctgatcga 6420
caagaccggc ttccatccga gtacgtgctc gctcgatgcg atgtttcgct tggtggtcga 6480
atgggcaggt agccggatca agcgtatgca gccgccgcat tgcatcagcc atgatggata 6540
ctttctcggc aggagcaagg tgagatgaca ggagatcctg ccccggcact tcgcccaata 6600
gcagccagtc ccttcccgct tcagtgacaa cgtcgagcac agctgcgcaa ggaacgcccg 6660
tcgtggccag ccacgatagc cgcgctgcct cgtcttgcag ttcattcagg gcaccggaca 6720
ggtcggtctt gacaaaaaga accgggcgcc cctgcgctga cagccggaac acggcggcat 6780
cagagcagcc gattgtctgt tgtgcccagt catagccgaa tagcctctcc acccaagcgg 6840
ccggagaacc tgcgtgcaat ccatcttgtt caattcgagt gcattcaaca tcagccatac 6900
tcttcctttt tcaatattat tgaagcattt atcagggtta ttgtctcatg agcggataca 6960
tatttgaatg tatttagaaa aataaacaaa taggggttcc gcgcacattt ccccgaaaag 7020
tgccac 7026

<210> SEQ ID NO 44
<211> LENGTH: 54
<212> TYPE: DNA
<213> ORGANISM: Artificial Sequence
<220> FEATURE:
<223> OTHER INFORMATION: Synthetic primer

<400> SEQUENCE: 44
ttaaacacta tatcaataga aacaatggca acattaaaag atcaactaat ccag 54

<210> SEQ ID NO 45
<211> LENGTH: 46
<212> TYPE: DNA
<213> ORGANISM: Artificial Sequence
<220> FEATURE:
<223> OTHER INFORMATION: Synthetic primer

<400> SEQUENCE: 45
aggataagca gaaccgttag aattgtaatt ccttttggat gcccca 46

<210> SEQ ID NO 46
<211> LENGTH: 7924
<212> TYPE: DNA
<213> ORGANISM: Artificial Sequence
<220> FEATURE:
<223> OTHER INFORMATION: Synthetic MD1188 vector

<400> SEQUENCE: 46
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtacgcatt taagcataaa cacgcactat gccgttcttc tcatgtatat 180
atatatacag gcaacacgca gatataggtg cgacgtgaac agtgagctgt atgtgcgcag 240
ctcgcgttgc attttcggaa gcgctcgttt tcggaaacgc tttgaagttc ctattccgaa 300
gttcctattc tctagctaga aagtatagga acttcagagc gcttttgaaa accaaaagcg 360
ctctgaagac gcactttcaa aaaaccaaaa acgcaccgga ctgtaacgag ctactaaaat 420
attgcgaata ccgcttccac aaacattgct caaaagtatc tctttgctat atatctctgt 480
gctatatccc tatataacct acccatccac ctttcgctcc ttgaacttgc atctaaactc 540
gacctctaca tttttatgt ttatctctag tattactctt tagacaaaaa aattgtagta 600
agaactattc atagagtgaa tcgaaaacaa tacgaaaatg taaacatttc ctatacgtag 660
tatatagaga caaaatagaa gaaaccgttc ataattttct gaccaatgaa gaatcatcaa 720
cgctatcact ttctgttcac aaagtatgcg caatccacat cggtatagaa tataatcggg 780
gatgccttta tcttgaaaaa atgcacccgc agcttcgcta gtaatcagta aacgcgggaa 840
gtggagtcag gcttttttta tggaagagaa aatagacacc aaagtagcct tcttctaacc 900
ttaacggacc tacagtgcaa aaagttatca agagactgca ttatagagcg cacaaaggag 960
aaaaaaagta atctaagatg ctttgttaga aaaatagcgc tctcgggatg catttttgta 1020
gaacaaaaaa gaagtataga ttctttgttg gtaaaatagc gctctcgcgt tgcatttctg 1080
ttctgtaaaa atgcagctca gattctttgt ttgaaaaatt agcgctctcg cgttgcattt 1140
ttgttttaca aaaatgaagc acagattctt cgttggtaaa atagcgcttt cgcgttgcat 1200
ttctgttctg taaaaatgca gctcagattc tttgtttgaa aaattagcgc tctcgcgttg 1260
catttttgtt ctacaaaatg aagcacagat gcttcgttaa tgtgctgcaa ggcgattaag 1320
ttgggtaacg ccagggtttt cccagtcacg acgttgtaaa acgacggcca gtgaattgta 1380
atacgactca ctatagggcg aattggactg taccgaatat ctgtgtccta atgaattcct 1440
cgttagtggt cattattata tacgatagtt gtagttttcc ctgttttccc tttgttcctt 1500
tttttcgagt ctagtattta ccaatataga agaaagagaa aataaataag gtttcttgtt 1560
agagattagt tacttttgct attattatcg caaattcctc ttccactata caaacaagaa 1620
agtaattact actcttattg taagatagta tgataatttc gacgatagat aatatttgct 1680
tttcgttggc cttttctttt ttttttcct tccttccctt cgaagatcct cccgtataat 1740
aacgccgcca gaccatgtag ggtaaccaga gaatacgccc actccgcttt cgcatgtggc 1800
actcctgtat gtcaaaatgc cgaataatct ccatccatga cgaagcgctt tgaggtgttt 1860
aattatatac agggcaaagt cttggagata aagaacgctt tcctaacaac ttgcgctatt 1920

-continued

```
cctcttattt ccttcaatcg attaaaatta acttttaatc gacattgtct tttaaaccag   1980
ggcaaagcaa aataaaagaa acttaatacg ttatgccgta atgaagggct accaaaaacg   2040
ataatctcaa ctgtaaacag gtacaatgcg gacccttttg ccacaaaaca tacatcattc   2100
attgccggaa aaagaaagaa gtgaagacag cagtgcagcc agccatgttg cgccaatcta   2160
attatagatg ctggtgccct gaggatgtat ctggagccag ccatggcatc atgcgctacc   2220
gccggatgta aaatccgaca cgcaaaagaa aaccttcgag gttgcgcact tcgcccaccc   2280
atgaaccaca cggttagtcc aaaaggggca gttcagattc cagatgcggg aattagcttg   2340
ctgccaccct cacctcacta acgctgcggt gtgcggatac ttcatgctat ttatagacgc   2400
gcgtgtcgga atcagcacgc gcaagaacca aatgggaaaa tcggaatggg tccagaactg   2460
ctttgagtgc tggctattgg cgtctgattt ccgttttggg aatcctttgc cgcgcgcccc   2520
tctcaaaact ccgcacaagt cccagaaagc gggaaagaaa taaaacgcca ccaaaaaaaa   2580
aaaaataaaa gccaatcctc gaagcgtggg tggtaggccc tggattatcc cgtacaagta   2640
tttctcagga gtaaaaaaac cgtttgtttt ggaattcccc atttcgcggc cacctacgcc   2700
gctatctttg caacaactat ctgcgataac tcagcaaatt ttgcatattc gtgttgcagt   2760
attgcgataa tgggagtctt acttccaaca taacggcaga aagaaatgtg agaaaatttt   2820
gcatcctttg cctccgttca agtatataaa gtcggcatgc ttgataatct ttctttccat   2880
cctacattgt tctaattatt cttattctcc tttattcttt cctaacatac caagaaatta   2940
atcttctgtc attcgcttaa acactatatc aatagaaaca atggcaacat taaaagatca   3000
actaatccag aatttgttga aagaggagca tgttccacaa aacaaaatca caatcgtcgg   3060
cgtaggtgca gtaggtatgg cttgtgccat atccatcttg atgaaagact tagctgatga   3120
ggtcgcgctg gttgatgtaa tggaggacaa acttaaagga gaaatgatgg atcttcaaca   3180
tggttcactc tttttgagaa ctcctaaaat tgtatccggg aaagattata acgttaccgc   3240
caattctaga cttgttataa tcacggctgg tgcaagacaa caggaaggcg aatcaagact   3300
taacttagtt cagagaaacg taaacatttt caagtttatc atcccaaata ttgtaaaata   3360
ctccccaaat tgcaagttgc tggttgtttc aaatcctgtt gacatattga cttacgttgc   3420
ttggaagatt tcaggtttcc caaagaatag agtaatcgga tctggttgca atctcgattc   3480
tgctcgtttt aggtatctga tgggtgaaag attaggggtt catccattga gttgtcacgg   3540
atggattcta ggtgaacatg gagatagttc tgtgcctgtt tggtcaggtg tcaacgtagc   3600
aggtgtctct ttgaaaaatc tacacccaga actaggaaca gatgccgaca aggaacaatg   3660
gaaggccgtc cacaaacaag tggtggattc tgcctacgaa gtcatcaaat tgaagggcta   3720
cacatcttgg gcaattggct tatccgtcgc tgatctggct gaatcaataa tgaaaaacct   3780
ccgtagagtg catcctataa gtactatgat taagggttta tacgggatca aggaagatgt   3840
ttttctatct gtgccatgta ttttgggcca aaatggaatt tctgacgttg ttaaagtgac   3900
acttactcat gaagaggaag cgtgtttgaa aaagagcgca gacaccttat ggggcatcca   3960
aaaggaatta caattctaac ggttctgctt atccttacga cgtgcctgac tacgcctgaa   4020
cccgatgcaa atgagacgat cgtctattcc tggtccggtt ttctctgccc tctcttctat   4080
tcactttttt tatactttat ataaaattat ataaatgaca taactgaaac gccacacgtc   4140
ctctcctatt cgttaacgcc tgtctgtagc gctgttactg aagctgcgca agtagttttt   4200
tcaccgtata ggccctcttt ttctctctct ttctttctct cccgcgctga tctcttcttc   4260
gaaacacaga gtgcaccata ccaccttttc aattcatcat ttttttttta ttcttttttt   4320
```

-continued tgatttcggt ttccttgaaa ttttttttgat tcggtaatct ccgaacagaa ggaagaacga 4380
aggaaggagc acagacttag attggtatat atacgcatat gtagtgttga agaaacatga 4440
aattgcccag tattcttaac ccaactgcac agaacaaaaa cctccaggaa acgaagataa 4500
atcatgtcga aagctacata taaggaacgt gctgctactc atcctagtcc tgttgctgcc 4560
aagctattta atatcatgca cgaaaagcaa acaaacttgt gtgcttcatt ggatgttcgt 4620
accaccaagg aattactgga gttagttgaa gcattaggtc ccaaaatttg tttactaaaa 4680
acacatgtgg atatcttgac tgatttttcc atggagggca cagttaagcc gctaaaggca 4740
ttatccgcca agtacaattt tttactcttc gaagacagaa aatttgctga cattggtaat 4800
acagtcaaat tgcagtactc tgcgggtgta tacagaatag cagaatgggc agacattacg 4860
aatgcacacg gtgtggtggg cccaggtatt gttagcggtt tgaagcaggc ggcagaagaa 4920
gtaacaaagg aacctagagg ccttttgatg ttagcagaat tgtcatgcaa gggctcccta 4980
tctactggag aatatactaa gggtactgtt gacattgcga agagcgacaa agattttgtt 5040
atcggcttta ttgctcaaag agacatgggt ggaagagatg aaggttacga ttggttgatt 5100
atgacacccg gtgtgggttt agatgacaag ggagacgcat tgggtcaaca gtatagaacc 5160
gtggatgatg tggtctctac aggatctgac attattattg ttggaagagg actatttgca 5220
aagggaaggg atgctaaggt agagggtgaa cgttacagaa aagcaggctg ggaagcatat 5280
ttgagaagat gcggccagca aaactaatca tgtaattagt tatgtcacgc ttacattcac 5340
gccctccccc cacatccgct ctaaccgaaa aggaaggagt tagacaacct gaagtctagg 5400
tccctattta tttttttata gttatgttag tattaagaac gttatttata tttcaaattt 5460
ttcttttttt tctgtacaga cgcgtgtacg catgtaacat tatactgaaa accttgcttg 5520
agaaggtttt gggacgctcg aaggctttaa tttgcgtctg tagcgctgtt actgaagctg 5580
cgcaagtagt tttttcaccg tataggccct ctttttctct ctctttcttt ctctcccgcg 5640
ctgatctctt cttcgaaaca tcatgaataa aaagaaaaag gaaatcaaga aaaaaaagcc 5700
ataatttatc ccacattttt ttttattgtc gctgttcaca ccgcataacg aagatattgg 5760
ctagctaacc agcttttgtt ccctttagtg agggttaatt tcgagcttgg cgtaatcatg 5820
gtcatagctg tttcctgtgt gaaattgtta tccgctcaca attccacaca acatacgagc 5880
cggaagcata aagtgtaaag cctggggtgc ctaatgagtg agctaactca cattaattgc 5940
gttgcgctca ctgcccgctt tccagtcggg aaacctgtcg tgccagctgc attaatgaat 6000
cggccaacgc gcggggagag gcggtttgcg tattgggcgc tcttccgctt cctcgctcac 6060
tgactcgctg cgctcggtcg ttcggctgcg gcgagcggta tcagctcact caaaggcggt 6120
aatacggtta tccacagaat caggggataa cgcaggaaag aacatgtgag caaaaggcca 6180
gcaaaaggcc aggaaccgta aaaaggccgc gttgctggcg tttttccata ggctccgccc 6240
ccctgacgag catcacaaaa atcgacgctc aagtcagagg tggcgaaacc cgacaggact 6300
ataaagatac caggcgtttc cccctggaag ctccctcgtg cgctctcctg ttccgaccct 6360
gccgcttacc ggatacctgt ccgcctttct cccttcggga agcgtggcgc tttctcatag 6420
ctcacgctgt aggtatctca gttcggtgta ggtcgttcgc tccaagctgg gctgtgtgca 6480
cgaacccccc gttcagcccg accgctgcgc cttatccggt aactatcgtc ttgagtccaa 6540
cccggtaaga cacgacttat cgccactggc agcagccact ggtaacagga ttagcagagc 6600
gaggtatgta ggcggtgcta cagagttctt gaagtggtgg cctaactacg gctacactag 6660

```
aaggacagta tttggtatct gcgctctgct gaagccagtt accttcggaa aaagagttgg   6720
tagctcttga tccggcaaac aaaccaccgc tggtagcggt ggtttttttg tttgcaagca   6780
gcagattacg cgcagaaaaa aaggatctca agaagatcct ttgatctttt ctacggggtc   6840
tgacgctcag tggaacgaaa actcacgtta agggattttg gtcatgagat tatcaaaaag   6900
gatcttcacc tagatccttt taaattaaaa atgaagtttt aaatcaatct aaagtatata   6960
tgagtaaact tggtctgaca tcagaagaac tcgtcaagaa ggcgatagaa ggcgatgcgc   7020
tgcgaatcgg gagcggcgat accgtaaagc acgaggaagc ggtcagccca ttcgccgcca   7080
agctcttcag caatatcacg ggtagccaac gctatgtcct gatagcggtc cgccacaccc   7140
agccggccac agtcgatgaa tccagaaaag cggccatttt ccaccatgat attcggcaag   7200
caggcatcgc catgggtcac gacgagatcc tcgccgtcgg gcatgctcgc cttgagcctg   7260
gcgaacagtt cggctggcgc gagcccctga tgctcttcgt ccagatcatc ctgatcgaca   7320
agaccggctt ccatccgagt acgtgctcgc tcgatgcgat gtttcgcttg gtggtcgaat   7380
gggcaggtag ccggatcaag cgtatgcagc cgccgcattg catcagccat gatggatact   7440
ttctcggcag gagcaaggtg agatgacagg agatcctgcc ccggcacttc gcccaatagc   7500
agccagtccc ttcccgcttc agtgacaacg tcgagcacag ctgcgcaagg aacgcccgtc   7560
gtggccagcc acgatagccg cgctgcctcg tcttgcagtt cattcagggc accggacagg   7620
tcggtcttga caaaaagaac cgggcgcccc tgcgctgaca gccggaacac ggcggcatca   7680
gagcagccga ttgtctgttg tgcccagtca tagccgaata gcctctccac ccaagcggcc   7740
ggagaacctg cgtgcaatcc atcttgttca attcgagtgc attcaacatc agccatactc   7800
ttcctttttc aatattattg aagcatttat cagggttatt gtctcatgag cggatacata   7860
tttgaatgta tttagaaaaa taaacaaata ggggttccgc gcacatttcc ccgaaaagtg   7920
ccac                                                                7924
```

<210> SEQ ID NO 47
<211> LENGTH: 7924
<212> TYPE: DNA
<213> ORGANISM: Artificial Sequence
<220> FEATURE:
<223> OTHER INFORMATION: Synthetic MD1189 vector

<400> SEQUENCE: 47

```
ctaaattgta agcgttaata ttttgttaaa attcgcgtta aatttttgtt aaatcagctc     60
atttttaac caataggccg aaatcggcaa aatcccttat aaatcaaaag aatagaccga     120
gatagggttg agtacgcatt taagcataaa cacgcactat gccgttcttc tcatgtatat    180
atatatacag gcaacacgca gatataggtg cgacgtgaac agtgagctgt atgtgcgcag    240
ctcgcgttgc attttcggaa gcgctcgttt tcggaaacgc tttgaagttc ctattccgaa    300
gttcctattc tctagctaga aagtatagga acttcagagc gcttttgaaa accaaaagcg    360
ctctgaagac gcactttcaa aaaaccaaaa acgcaccgga ctgtaacgag ctactaaaat    420
attgcgaata ccgcttccac aaacattgct caaaagtatc tctttgctat atatctctgt    480
gctatatccc tatataacct acccatccac ctttcgctcc ttgaacttgc atctaaactc    540
gacctctaca ttttttatgt ttatctctag tattactctt tagacaaaaa aattgtagta    600
agaactattc atagagtgaa tcgaaaacaa tacgaaaatg taaacatttc ctatacgtag    660
tatatagaga caaaatagaa gaaaccgttc ataattttct gaccaatgaa gaatcatcaa    720
cgctatcact ttctgttcac aaagtatgcg caatccacat cggtatagaa tataatcggg    780
```

-continued

```
gatgccttta tcttgaaaaa atgcacccgc agcttcgcta gtaatcagta aacgcgggaa    840
gtggagtcag gcttttttta tggaagagaa aatagacacc aaagtagcct tcttctaacc    900
ttaacggacc tacagtgcaa aaagttatca agagactgca ttatagagcg cacaaaggag    960
aaaaaaagta atctaagatg ctttgttaga aaaatagcgc tctcgggatg catttttgta   1020
gaacaaaaaa gaagtataga ttctttgttg gtaaaatagc gctctcgcgt tgcatttctg   1080
ttctgtaaaa atgcagctca gattctttgt ttgaaaaatt agcgctctcg cgttgcattt   1140
ttgttttaca aaaatgaagc acagattctt cgttggtaaa atagcgcttt cgcgttgcat   1200
ttctgttctg taaaaatgca gctcagattc tttgtttgaa aaattagcgc tctcgcgttg   1260
catttttgtt ctacaaaatg aagcacagat gcttcgttaa tgtgctgcaa ggcgattaag   1320
ttgggtaacg ccagggtttt cccagtcacg acgttgtaaa acgacggcca gtgaattgta   1380
atacgactca ctatagggcg aattggactg taccgaatat ctgtgtccta atgaattcct   1440
cgttagtggt cattattata tacgatagtt gtagttttcc ctgttttccc tttgttcctt   1500
tttttcgagt ctagtattta ccaatataga agaaagagaa aataaataag gtttcttgtt   1560
agagattagt tacttttgct attattatcg caaattcctc ttccactata caaacaagaa   1620
agtaattact actcttattg taagatagta tgataatttc gacgatagat aatatttgct   1680
tttcgttggc cttttctttt ttttttttcct tccttccctt cgaagatcct cccgtataat   1740
aacgccgcca gaccatgtag ggtaaccaga gaatacgccc actccgcttt cgcatgtggc   1800
actcctgtat gtcaaaatgc cgaataatct ccatccatga cgaagcgctt tgaggtgttt   1860
aattatatac agggcaaagt cttggagata aagaacgctt tcctaacaac ttgcgctatt   1920
cctcttattt ccttcaatcg attaaaatta acttttaatc gacattgtct tttaaaccag   1980
ggcaaagcaa aataaaagaa acttaatacg ttatgccgta atgaagggct accaaaaacg   2040
ataatctcaa ctgtaaacag gtacaatgcg gacccttttg ccacaaaaca tacatcattc   2100
attgccggaa aaagaaagaa gtgaagacag cagtgcagcc agccatgttg cgccaatcta   2160
attatagatg ctggtgccct gaggatgtat ctggagccag ccatggcatc atgcgctacc   2220
gccggatgta aaatccgaca cgcaaaagaa aaccttcgag gttgcgcact tcgcccaccc   2280
atgaaccaca cggttagtcc aaaaggggca gttcagattc cagatgcggg aattagcttg   2340
ctgccaccct cacctcacta acgctgcggt gtgcggatac ttcatgctat ttatagacgc   2400
gcgtgtcgga atcagcacgc gcaagaacca aatgggaaaa tcggaatggg tccagaactg   2460
ctttgagtgc tggctattgg cgtctgattt ccgttttggg aatcctttgc cgcgcgcccc   2520
tctcaaaact ccgcacaagt cccagaaagc gggaaagaaa taaaacgcca ccaaaaaaaa   2580
aaaaataaaa gccaatcctc gaagcgtggg tggtaggccc tggattatcc cgtacaagta   2640
tttctcagga gtaaaaaaac cgtttgtttt ggaattcccc atttcgcggc cacctacgcc   2700
gctatctttg caacaactat ctgcgataac tcagcaaatt ttgcatattc gtgttgcagt   2760
attgcgataa tgggagtctt acttccaaca taacggcaga aagaaatgtg agaaaatttt   2820
gcatcctttg cctccgttca agtatataaa gtcggcatgc ttgataatct ttctttccat   2880
cctacattgt tctaattatt cttattctcc tttattcttt cctaacatac caagaaatta   2940
atcttctgtc attcgcttaa acactatatc aatagaaaca atggcaacat taaaagatca   3000
actaatccag aatttgttga aagaggagca tgttccacaa aacaaaatca caatcgtcgg   3060
cgtaggtgca gtaggtatgg cttgtgccat atccatcttg atgaaagact tagctgatga   3120
```

```
ggtcgcgctg gttgatgtaa tggaggacaa acttaaagga gaaatgatgg atcttcaaca   3180
tggttcactc tttttgagaa ctcctaaaat tgtatccggg aaagattata acgttaccgc   3240
caattctaga cttgttataa tcacggctgg tgcaagacaa caggaaggcg aatcaagact   3300
taacttagtt cagagaaacg taaacatttt caagtttatc atcccaaata ttgtaaaata   3360
ctccccaaat tgcaagttgc tggttgtttc aaatcctgtt gacatattga cttacgttgc   3420
ttggaagatt tcaggtttcc caaagaatag agtaatcgga tctggttgca atctcgattc   3480
tgctcgtttt aggtatctga tgggtgaaag attaggggtt catccattga gttgtcacgg   3540
atggattcta ggtgaacatg gagatagttc tgtgcctgtt tggtcaggtg tcaacgtagc   3600
aggtgtctct ttgaaaaatc tacacccaga actaggaaca gatgccgaca aggaacaatg   3660
gaaggccgtc cacaaacaag tggtgggttc tgcctacgaa gtcatcaaat tgaagggcta   3720
cacatcttgg gcaattggct tatccgtcgc tgatctggct gaatcaataa tgaaaaacct   3780
ccgtagagtg catcctataa gtactatgat taagggttta tacgggatca aggaagatgt   3840
tttctatct gtgccatgta ttttgggcca aaatggaatt tctgacgttg ttaaagtgac   3900
acttactcat gaagaggaag cgtgtttgaa aaagagcgca gacaccttat ggggcatcca   3960
aaaggaatta caattctaac ggttctgctt atccttacga cgtgcctgac tacgcctgaa   4020
cccgatgcaa atgagacgat cgtctattcc tggtccggtt ttctctgccc tctcttctat   4080
tcactttttt tatactttat ataaaattat ataaatgaca taactgaaac gccacacgtc   4140
ctctcctatt cgttaacgcc tgtctgtagc gctgttactg aagctgcgca agtagttttt   4200
tcaccgtata ggccctcttt ttctctctct ttctttctct cccgcgctga tctcttcttc   4260
gaaacacaga gtgcaccata ccaccttttc aattcatcat ttttttttta ttcttttttt   4320
tgatttcggt ttccttgaaa tttttttgat tcggtaatct ccgaacagaa ggaagaacga   4380
aggaaggagc acagacttag attggtatat atacgcatat gtagtgttga agaaacatga   4440
aattgcccag tattcttaac ccaactgcac agaacaaaaa cctccaggaa acgaagataa   4500
atcatgtcga aagctacata taaggaacgt gctgctactc atcctagtcc tgttgctgcc   4560
aagctattta atatcatgca cgaaaagcaa acaaacttgt gtgcttcatt ggatgttcgt   4620
accaccaagg aattactgga gttagttgaa gcattaggtc ccaaaatttg tttactaaaa   4680
acacatgtgg atatcttgac tgatttttcc atggagggca cagttaagcc gctaaaggca   4740
ttatccgcca agtacaattt tttactcttc gaagacagaa aatttgctga cattggtaat   4800
acagtcaaat tgcagtactc tgcgggtgta tacagaatag cagaatgggc agacattacg   4860
aatgcacacg gtgtggtggg cccaggtatt gttagcggtt tgaagcaggc ggcagaagaa   4920
gtaacaaagg aacctagagg ccttttgatg ttagcagaat tgtcatgcaa gggctcccta   4980
tctactggag aatatactaa gggtactgtt gacattgcga agagcgacaa agattttgtt   5040
atcggcttta ttgctcaaag agacatgggt ggaagagatg aaggttacga ttggttgatt   5100
atgacacccg gtgtgggttt agatgacaag ggagacgcat tgggtcaaca gtatagaacc   5160
gtggatgatg tggtctctac aggatctgac attattattg ttggaagagg actatttgca   5220
aagggaaggg atgctaaggt agagggtgaa cgttacagaa aagcaggctg ggaagcatat   5280
ttgagaagat gcggccagca aaactaatca tgtaattagt tatgtcacgc ttacattcac   5340
gccctccccc cacatccgct ctaaccgaaa aggaaggagt tagacaacct gaagtctagg   5400
tccctattta ttttttttata gttatgttag tattaagaac gttatttata tttcaaattt   5460
ttcttttttt tctgtacaga cgcgtgtacg catgtaacat tatactgaaa accttgcttg   5520
```

```
agaaggtttt gggacgctcg aaggctttaa tttgcgtctg tagcgctgtt actgaagctg   5580
cgcaagtagt tttttcaccg tataggccct ctttttctct ctctttcttt ctctcccgcg   5640
ctgatctctt cttcgaaaca tcatgaataa aaagaaaaag gaaatcaaga aaaaaaagcc   5700
ataatttatc ccacattttt ttttattgtc gctgttcaca ccgcataacg aagatattgg   5760
ctagctaacc agcttttgtt ccctttagtg agggttaatt tcgagcttgg cgtaatcatg   5820
gtcatagctg tttcctgtgt gaaattgtta tccgctcaca attccacaca acatacgagc   5880
cggaagcata aagtgtaaag cctggggtgc ctaatgagtg agctaactca cattaattgc   5940
gttgcgctca ctgcccgctt tccagtcggg aaacctgtcg tgccagctgc attaatgaat   6000
cggccaacgc gcggggagag gcggtttgcg tattgggcgc tcttccgctt cctcgctcac   6060
tgactcgctg cgctcggtcg ttcggctgcg gcgagcggta tcagctcact caaaggcggt   6120
aatacggtta tccacagaat caggggataa cgcaggaaag aacatgtgag caaaaggcca   6180
gcaaaaggcc aggaaccgta aaaaggccgc gttgctggcg tttttccata ggctccgccc   6240
ccctgacgag catcacaaaa atcgacgctc aagtcagagg tggcgaaacc cgacaggact   6300
ataaagatac caggcgtttc cccctggaag ctccctcgtg cgctctcctg ttccgaccct   6360
gccgcttacc ggatacctgt ccgcctttct cccttcggga agcgtggcgc tttctcatag   6420
ctcacgctgt aggtatctca gttcggtgta ggtcgttcgc tccaagctgg gctgtgtgca   6480
cgaacccccc gttcagcccg accgctgcgc cttatccggt aactatcgtc ttgagtccaa   6540
cccggtaaga cacgacttat cgccactggc agcagccact ggtaacagga ttagcagagc   6600
gaggtatgta ggcggtgcta cagagttctt gaagtggtgg cctaactacg gctacactag   6660
aaggacagta tttggtatct gcgctctgct gaagccagtt accttcggaa aaagagttgg   6720
tagctcttga tccggcaaac aaaccaccgc tggtagcggt ggtttttttg tttgcaagca   6780
gcagattacg cgcagaaaaa aaggatctca agaagatcct ttgatctttt ctacggggtc   6840
tgacgctcag tggaacgaaa actcacgtta agggattttg gtcatgagat tatcaaaaag   6900
gatcttcacc tagatccttt taaattaaaa atgaagtttt aaatcaatct aaagtatata   6960
tgagtaaact tggtctgaca tcagaagaac tcgtcaagaa ggcgatagaa ggcgatgcgc   7020
tgcgaatcgg gagcggcgat accgtaaagc acgaggaagc ggtcagccca ttcgccgcca   7080
agctcttcag caatatcacg ggtagccaac gctatgtcct gatagcggtc cgccacaccc   7140
agccggccac agtcgatgaa tccagaaaag cggccatttt ccaccatgat attcggcaag   7200
caggcatcgc catgggtcac gacgagatcc tcgccgtcgg gcatgctcgc cttgagcctg   7260
gcgaacagtt cggctggcgc gagcccctga tgctcttcgt ccagatcatc ctgatcgaca   7320
agaccggctt ccatccgagt acgtgctcgc tcgatgcgat gtttcgcttg gtggtcgaat   7380
gggcaggtag ccggatcaag cgtatgcagc cgccgcattg catcagccat gatggatact   7440
ttctcggcag gagcaaggtg agatgacagg agatcctgcc ccggcacttc gcccaatagc   7500
agccagtccc ttcccgcttc agtgacaacg tcgagcacag ctgcgcaagg aacgcccgtc   7560
gtggccagcc acgatagccg cgctgcctcg tcttgcagtt cattcagggc accggacagg   7620
tcggtcttga caaaaagaac cgggcgcccc tgcgctgaca gccggaacac ggcggcatca   7680
gagcagccga ttgtctgttg tgcccagtca tagccgaata gcctctccac ccaagcggcc   7740
ggagaacctg cgtgcaatcc atcttgttca attcgagtgc attcaacatc agccatactc   7800
ttcctttttc aatattattg aagcatttat cagggttatt gtctcatgag cggatacata   7860
```

tttgaatgta tttagaaaaa taaacaaata ggggttccgc gcacatttcc ccgaaaagtg 7920
ccac 7924

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
ttgcataata ttgtccgctg 20

<210> SEQ ID NO 49
<211> LENGTH: 61
<212> TYPE: DNA
<213> ORGANISM: Artificial Sequence
<220> FEATURE:
<223> OTHER INFORMATION: Synthetic primer

<400> SEQUENCE: 49
ccaattcgcc ctatagtgag tcgtattaca gggaacaaac ccaaatctga ttccaaggag 60
a 61

<210> SEQ ID NO 50
<211> LENGTH: 57
<212> TYPE: DNA
<213> ORGANISM: Artificial Sequence
<220> FEATURE:
<223> OTHER INFORMATION: Synthetic primer

<400> SEQUENCE: 50
agcttttgtt ccctttagtg agggttaatt ctgttgaatt ggcttaagtc tgggtcc 57

<210> SEQ ID NO 51
<211> LENGTH: 22
<212> TYPE: DNA
<213> ORGANISM: Artificial Sequence
<220> FEATURE:
<223> OTHER INFORMATION: Synthetic primer

<400> SEQUENCE: 51
gtgtctagtc ttctattacg ct 22

<210> SEQ ID NO 52
<211> LENGTH: 19
<212> TYPE: DNA
<213> ORGANISM: Artificial Sequence
<220> FEATURE:
<223> OTHER INFORMATION: Synthetic primer

<400> SEQUENCE: 52
ttgagataag cacactgca 19

<210> SEQ ID NO 53
<211> LENGTH: 20
<212> TYPE: DNA
<213> ORGANISM: Artificial Sequence
<220> FEATURE:
<223> OTHER INFORMATION: Synthetic primer

<400> SEQUENCE: 53
caacatcacc caattcatcg 20

<210> SEQ ID NO 54
<211> LENGTH: 332
<212> TYPE: PRT
<213> ORGANISM: Bos Taurus

<400> SEQUENCE: 54

```
Met Ala Thr Leu Lys Asp Gln Leu Ile Gln Asn Leu Leu Lys Glu Glu
  1               5                  10                  15

His Val Pro Gln Asn Lys Ile Thr Ile Val Gly Val Gly Ala Val Gly
             20                  25                  30

Met Ala Cys Ala Ile Ser Ile Leu Met Lys Asp Leu Ala Asp Glu Val
         35                  40                  45

Ala Leu Val Asp Val Met Glu Asp Lys Leu Lys Gly Glu Met Met Asp
     50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Arg Leu Val Ile Ile Thr Ala
                85                  90                  95

Gly Ala Arg Gln Gln Glu Gly Glu Ser Arg Leu Gly Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr His Glu Glu Glu Ala Cys Leu Lys Lys Ser Ala
305                 310                 315                 320

Asp Thr Leu Trp Gly Ile Gln Lys Glu Leu Gln Phe
                325                 330
```

<210> SEQ ID NO 55
<211> LENGTH: 332
<212> TYPE: PRT
<213> ORGANISM: Bos Taurus

<400> SEQUENCE: 55

```
Met Ala Thr Leu Lys Asp Gln Leu Ile Gln Asn Leu Leu Lys Glu Glu
```

-continued

```
 1               5                  10                  15

His Val Pro Gln Asn Lys Ile Thr Ile Val Gly Val Gly Ala Val Gly
            20                  25                  30

Met Ala Cys Ala Ile Ser Ile Leu Met Lys Asp Leu Ala Asp Glu Val
        35                  40                  45

Ala Leu Val Asp Val Met Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Arg Leu Val Ile Ile Thr Ala
                85                  90                  95

Gly Ala Arg Gln Gln Glu Gly Glu Ser Arg Leu Leu Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr His Glu Glu Glu Ala Cys Leu Lys Lys Ser Ala
305                 310                 315                 320

Asp Thr Leu Trp Gly Ile Gln Lys Glu Leu Gln Phe
                325                 330
```

<210> SEQ ID NO 56
<211> LENGTH: 999
<212> TYPE: DNA
<213> ORGANISM: Bos Taurus

<400> SEQUENCE: 56

```
atggcaacat taaaagatca actaatccag aatttgttga aagaggagca tgttccacaa      60

aacaaaatca caatcgtcgg cgtaggtgca gtaggtatgg cttgtgccat atccatcttg     120

atgaaagact tagctgatga ggtcgcgctg gttgatgtaa tggaggacaa acttaaagga     180

gaaatgatgg atcttcaaca tggttcactc tttttgagaa ctcctaaaat tgtatccggg     240

aaagattata acgttaccgc caattctaga cttgttataa tcacggctgg tgcaagacaa     300
```

caggaaggcg aatcaagact tggcttagtt cagagaaacg taaacatttt caagtttatc 360
atcccaaata ttgtaaaata ctccccaaat tgcaagttgc tggttgtttc aaatcctgtt 420
gacatattga cttacgttgc ttggaagatt tcaggtttcc caaagaatag agtaatcgga 480
tctggttgca atctcgattc tgctcgtttt aggtatctga tgggtgaaag attaggggtt 540
catccattga gttgtcacgg atggattcta ggtgaacatg gagatagttc tgtgcctgtt 600
tggtcaggtg tcaacgtagc aggtgtctct ttgaaaaatc tacacccaga actaggaaca 660
gatgccgaca aggaacaatg gaaggccgtc cacaaacaag tggtggattc tgcctacgaa 720
gtcatcaaat tgaagggcta cacatcttgg gcaattggct tatccgtcgc tgatctggct 780
gaatcaataa tgaaaaacct ccgtagagtg catcctataa gtactatgat taagggttta 840
tacgggatca aggaagatgt ttttctatct gtgccatgta ttttgggcca aaatggaatt 900
tctgacgttg ttaaagtgac acttactcat gaagaggaag cgtgtttgaa aaagagcgca 960
gacaccttat ggggcatcca aaaggaatta caattctaa 999

<210> SEQ ID NO 57
<211> LENGTH: 999
<212> TYPE: DNA
<213> ORGANISM: Bos Taurus

<400> SEQUENCE: 57
atggcaacat taaaagatca actaatccag aatttgttga aagaggagca tgttccacaa 60
aacaaaatca caatcgtcgg cgtaggtgca gtaggtatgg cttgtgccat atccatcttg 120
atgaaagact tagctgatga ggtcgcgctg gttgatgtaa tggaggacaa acttaaagga 180
gaaatgatgg atcttcaaca tggttcactc tttttgagaa ctcctaaaat tgtatccggg 240
aaagattata acgttaccgc caattctaga cttgttataa tcacggctgg tgcaagacaa 300
caggaaggcg aatcaagact tttattagtt cagagaaacg taaacatttt caagtttatc 360
atcccaaata ttgtaaaata ctccccaaat tgcaagttgc tggttgtttc aaatcctgtt 420
gacatattga cttacgttgc ttggaagatt tcaggtttcc caaagaatag agtaatcgga 480
tctggttgca atctcgattc tgctcgtttt aggtatctga tgggtgaaag attaggggtt 540
catccattga gttgtcacgg atggattcta ggtgaacatg gagatagttc tgtgcctgtt 600
tggtcaggtg tcaacgtagc aggtgtctct ttgaaaaatc tacacccaga actaggaaca 660
gatgccgaca aggaacaatg gaaggccgtc cacaaacaag tggtggattc tgcctacgaa 720
gtcatcaaat tgaagggcta cacatcttgg gcaattggct tatccgtcgc tgatctggct 780
gaatcaataa tgaaaaacct ccgtagagtg catcctataa gtactatgat taagggttta 840
tacgggatca aggaagatgt ttttctatct gtgccatgta ttttgggcca aaatggaatt 900
tctgacgttg ttaaagtgac acttactcat gaagaggaag cgtgtttgaa aaagagcgca 960
gacaccttat ggggcatcca aaaggaatta caattctaa 999

<210> SEQ ID NO 58
<211> LENGTH: 31
<212> TYPE: DNA
<213> ORGANISM: Artificial Sequence
<220> FEATURE:
<223> OTHER INFORMATION: Synthetic primer

<400> SEQUENCE: 58
cgagctcttc gcggccacct acgccgctat c 31

-continued

```
<210> SEQ ID NO 59
<211> LENGTH: 32
<212> TYPE: DNA
<213> ORGANISM: Artificial Sequence
<220> FEATURE:
<223> OTHER INFORMATION: Synthetic primer

<400> SEQUENCE: 59

gctctagata ttgatatagt gtttaagcga at                          32


<210> SEQ ID NO 60
<211> LENGTH: 34
<212> TYPE: DNA
<213> ORGANISM: Artificial Sequence
<220> FEATURE:
<223> OTHER INFORMATION: Synthetic primer

<400> SEQUENCE: 60

aattgaattc atggcaacat taaaagatca acta                        34


<210> SEQ ID NO 61
<211> LENGTH: 35
<212> TYPE: DNA
<213> ORGANISM: Artificial Sequence
<220> FEATURE:
<223> OTHER INFORMATION: Synthetic primer

<400> SEQUENCE: 61

aattgtcgac ttagaattgt aattcctttt ggatg                       35


<210> SEQ ID NO 62
<211> LENGTH: 21
<212> TYPE: DNA
<213> ORGANISM: Artificial Sequence
<220> FEATURE:
<223> OTHER INFORMATION: Synthetic primer

<400> SEQUENCE: 62

actaaaggga acaaaagctg g                                      21


<210> SEQ ID NO 63
<211> LENGTH: 24
<212> TYPE: DNA
<213> ORGANISM: Artificial Sequence
<220> FEATURE:
<223> OTHER INFORMATION: Synthetic primer

<400> SEQUENCE: 63

gacataacta attacatgac tcga                                   24
```

LACTATE DEHYDROGENASE MUTANT, POLYNUCLEOTIDE CODING FOR THE MUTANT, YEAST CELL INCLUDING THE POLYNUCLEOTIDE, METHOD OF PREPARING THE MUTANT, AND METHOD OF PRODUCING THE LACTATE USING THE SAME

RELATED APPLICATION

This application claims the benefit of Korean Patent Application No. 10-2014-0017517, filed on Feb. 14, 2014, and Korean Patent Application No. 10-2014-0125301, filed on Sep. 19, 2014, in the Korean Intellectual Property Office, the entire disclosures of which are hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 90,442 bytes ASCII (Text) file named "716857_ST25.TXT," created Feb. 12, 2015.

BACKGROUND

1. Field

The present disclosure relates to a lactate dehydrogenase mutant, a polynucleotide coding for the mutant, a yeast cell including the polynucleotide encoding the mutant, a method of preparing the mutant, and a method of producing lactate by using the same.

2. Description of the Related Art

Lactate is an organic acid that is broadly used in various industrial fields, such as food, pharmaceutics, chemicals, and electronics. Lactate is colorless, odorless, and a low-volatile material that dissolves well in water. Lactate is non-toxic to the human body and thus may be used as a flavor agent, an acidifier, or a preservative. Additionally, in addition to being an environmentally-friendly alternative to a polymer material, lactate is a raw material of a polylactic acid (PLA), which is biodegradable plastic.

PLA is a polyester-based resin that is ring-open polymerized when converted into lactide, which is a dimer, for technical polymerization and may be variously processed into a film, sheet, fiber, plastic, and etc. Thus, the demand for PLA as bioplastic has recently increased to broadly replace conventional typical petrochemical plastic, such as polyethylene (PE), polypropylene (PP), polyethylene terephthalate (PET), or polystylene (PS).

In addition, lactate includes both a hydroxyl group and a carboxyl group and thus is highly reactive. Accordingly, lactate may easily be converted into an industrially important compound, such as lactate ester, acetaldehyde, or propyleneglycol, and thus has received attention in the chemical industry as an alternative chemical material of the next generation.

Currently, lactate is commercially produced through a petrochemical synthesis process and a biotechnical fermentation process. The petrochemical synthesis process includes oxidation of ethylene derived from crude oil, a hydrocyanation addition reaction via acetaldehyde to prepare lactonitrile, distillation to refine the same, and a hydrolysis reaction using hydrochloric acid or sulfuric acid. Additionally The biotechnical fermentation process may produce lactate by using a renewable carbohydrate material, such as starch, sucrose, maltose, glucose, fructose, and xylose, as a substrate.

Despite the availability of these processes, there remains a need for a method of efficiently preparing a lactate dehydrogenase mutant and a method of producing lactate by using the same are required.

SUMMARY

Provided are lactate dehydrogenase mutants having a catalytic activity for conversion of pyruvate into lactate.

Provided are polynucleotides coding for the lactate dehydrogenase mutants.

Provided are methods of preparing lactate dehydrogenase mutants having catalytic activity for conversion of pyruvate into lactate.

Provided are yeast cells including genes coding for the lactate dehydrogenase mutants.

Provided are methods of producing lactate by using yeast cells including the genes coding for the lactate dehydrogenase and/or lactate dehydrogenase mutants.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
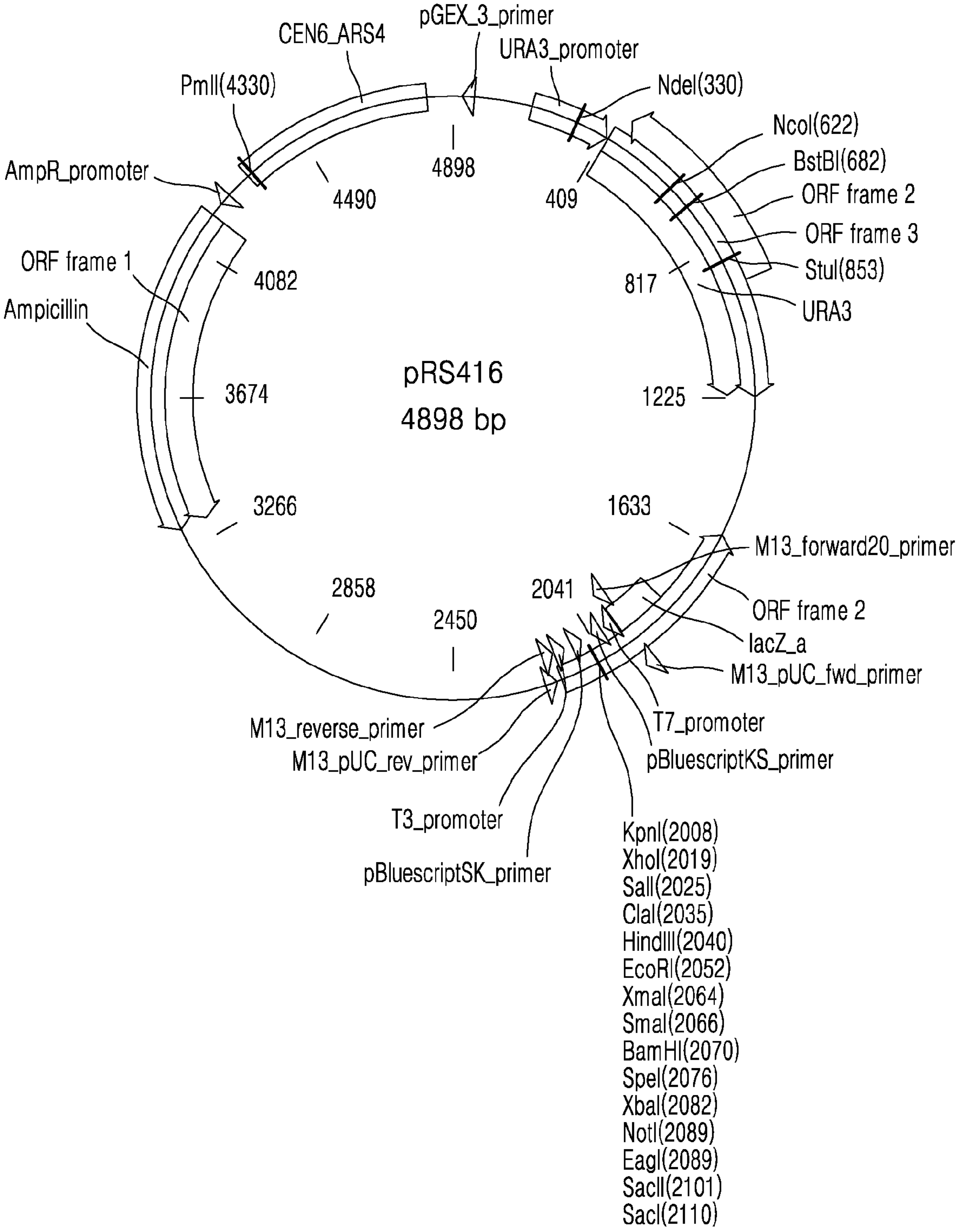
FIG. 1 is an illustration of a pRS416 vector.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the term "a sequence identity" of nucleic acid or polypeptide refers to the extent of identity between bases or amino acid residues of sequences after aligning the sequences such that they maximally match in certain comparative regions. The sequence identity is a value calculated by optimally aligning two sequences at certain comparative regions, wherein portions of the sequences at the certain comparative regions may be added or deleted, compared to reference sequences. A percentage of sequence identity may be calculated by, for example, comparing two optimally aligned sequences in the entire comparative region, determining the number of locations in which the same amino acids or nucleic acids appear to obtain the number of matched locations, dividing the number of matched locations by the total number of locations in the comparative region (that is, the size of the range), and multiplying by 100 to calculate the percentage of the sequence identity. The percentage of the sequence identity may be calculated by using a known sequence comparison program, and examples of such program include BLASTN (NCBI), CLC Main Workbench (CLC bio), and MegAlign™ (DNASTAR Inc).

Various levels of sequence identity may be used to identify various types of polypeptides or polynucleotides having the same or similar functions. For example, a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100% may be used.

As used herein, the term "lactate" refers to "lactic acid" or a salt thereof.

According to one aspect of the present invention, provided is a lactate dehydrogenase that converts pyruvate into lactate. A lactate dehydrogenase may be a wild-type lactate dehydrogenase mutant having an amino acid sequence of SEQ ID NO: 1. The lactate dehydrogenase may be a lactate dehydrogenase derived from *Bos Taurus*. As used herein the terms "mutant" and "mutated" and the like refer to amino acid residue modification, for example, the substitution of one amino acid within the sequence for another or the deletion or addition of one or more amino acid residues.

The lactate dehydrogenase mutant is a lactate dehydrogenase that has an amino acid sequence of SEQ ID NO: 1 and converts pyruvate into lactate, wherein at least one of the amino acid residues of a lactate dehydrogenase is mutated, and the mutation may occur at $102^{nd}$ position Glu of SEQ ID NO: 1, $108^{th}$ position Asn of SEQ ID NO: 1, $236^{th}$ position Asp of SEQ ID NO: 1, $237^{th}$ position Ser of SEQ ID NO: 1, or a combination thereof.

The lactate dehydrogenase may include $102^{nd}$ position Glu of SEQ ID NO: 1, $108^{th}$ position Asn of SEQ ID NO: 1, $236^{th}$ position Asp of SEQ ID NO: 1, $237^{th}$ position Ser of SEQ ID NO: 1, or a combination thereof substituted with a non-polar amino acid. The non-polar amino acid may be Gly, Ala, Leu, Ile, Val, Pro, or Met. In one embodiment, the lactate dehydrogenase may include $102^{nd}$ position Glu of SEQ ID NO: 1, $236^{th}$ position Asp of SEQ ID NO: 1, $237^{th}$ position Ser of SEQ ID NO: 1, or $108^{th}$ position Asn of SEQ ID NO: 1 substituted with Gly. In another embodiment, the lactate dehydrogenase may include $108^{th}$ position Asn of SEQ ID NO: 1 substituted with Leu. The lactate dehydrogenase may have each of amino acid sequences of SEQ ID NOS: 3, 4, 5, 54, and 55. Also, a gene encoding the lactate dehydrogenase may encode an amino acid sequence having a sequence identity of about 95% or more with an amino acid sequence of SEQ ID NO: 3, 4, 5, 54, or 55. The gene encoding the lactate dehydrogenase may have a sequence identity of about 95% or more with a polynucleotide sequence of SEQ ID NO: 6, 7, 8, 56, or 57.

When the lacatate dehydrogenase combines with a pyruvate, which is a substrate, a distance between a catalytic site of the lactate dehydrogenase and a pyruvate may be shortened compared to a distance between a catalytic site of a wild-type lactate dehydrogenase (e.g., SEQ ID NO: 1) and a pyruvate. The catalytic site of the lactate dehydrogenase may be $106^{th}$ position Arg of the SEQ ID NO: 1, $138^{th}$ position Asn of the SEQ ID NO: 1, $169^{th}$ position Arg of the SEQ ID NO: 1, $193^{th}$ position His of the SEQ ID NO: 1, $248^{th}$ position Thr of the SEQ ID NO: 1, or a combination thereof.

Also, the lactate dehydrogenase may have mutated amino acid residues, such that pKa of a proton donor residue may be increased compared to pKa of a proton donor residue of a wild-type lactate dehydrogenase (SEQ ID NO: 1).

The lactate dehydrogenase or a mutant thereof may be an enzyme for catalyzing a conversion of pyruvate into lactate. The lacatate dehydrogenase may be a NAD(P)-dependent enzyme, may act on pyruvate, and may produce L-lactate or D-lactate. The NAD(P)-dependent enzyme may be an enzyme classified as EC 1.1.1.27 producing L-lactate or an enzyme classified as EC 1.1.1.28 producing D-lactate. The enzyme classified as EC 1.1.1.27 may be L-lactate dehydrogenase and the enzyme classified as EC 1.1.1.28 may be D-lactate dehyrogenase.

The lactate dehydrogenase mutant may be mutated to have enhanced specific activity compared to a specific activity compared to a wild-type lactate dehydrogenase or a non-mutated lactate dehydrogenase. The specific activity of the mutant may be increased to be about 5% or greater, about 10% or greater, about 15% or greater, about 20% or greater, about 30% or greater, about 50% or greater, about 60% or greater, about 70% or greater, or about 100% or greater than the specific activity of the wild-type lactate dehydrogenase or the non-mutated lactate dehydrogenase. For example, the lactate dehydrogenase comprising SEQ ID NO: 1 including a mutation as described herein may have a specific activity that is increased to be about 0.020 U/mg or greater, about 0.025 U/mg or greater, about 0.030 U/mg or greater, or about 0.033 U/mg or greater than the wild-type lactate dehydrogenase or the non-mutated lactate dehydrogenase. The lactate dehydrogenase mutant may be modified such that the lactate dehydrogenase mutant has Km or Kcat that is improved compared to those of the non-mutated lactate dehydrogenase. The Km of the mutant may have a Km value that is about 1.5 times, about 2 times, about 3 times, or about 4 times as great as the Km of the non-mutated lactate dehydrogenase. The Kcat of the mutant may be about 1.5 times, about 2 times, or about 2.5 times as great as the Kcat of the non-mutated lactate dehydrogenase.

According to another aspect of the present invention, provided is a polynucleotide encoding a lactate dehydrogenase mutant as described herein.

As used herein, the term, "polynucleotide" broadly includes DNA and RNA molecules such as gDNA and cDNA, as well as a nucleotide, which is a basic unit of the polynucleotide, and may be a natural nucleotide as well as an analogue in which sugar or base is modified. The polynucleotide may be an isolated polynucleotide.

According to another aspect of the present invention, provided is a vector or an expression cassette including a polynucleotide coding for the lactate dehydrogenase. The polynucleotide may be operably linked to a regulatory sequence. The cassette may be a unit sequence from which protein operably linked to a regulatory sequence may be expressed. The regulatory sequence may include a promoter, a terminator, or an enhancer. The promoter may be operably linked to a sequence coding for a gene. The expression, "operably linked" may refer to a functional bond between a nucleic acid expression regulatory sequence and another nucleotide sequence. Due to such operable linkage, the regulatory sequence may control transcription and/or translation of the nucleotide sequence coding for the gene. The regulatory sequence may include a replication orgin, a promoter, a terminator, and/or an enhancer. The replication origin may include a yeast autonomous replication sequence (ARS). The yeast ARS may be stabilized by a yeast centrometric sequence (CEN). The promoter may operably combined with a sequence encoding a gene. The promoter may be selected from the group consisting of covalently linked cell wall protein 12 (CCW12), glyceraldehyde-3-phosphate dehydrogenase (GPD), pyruvate decarboxylase 1 (PDC1), phosphoglycerate kinase (PGK), transcription enhancer factor 1 (TEF1), glyceraldehyde-3-phosphate dehydrogenase (TDH), triose phosphate isomerase (TPI), purine-cytosine permease (PCPL3), and alcohol dehydrogenase (ADH) promoters derived from genes. The CCW12 promoter, CYC promoter, TEF1 promoter, PGK1 promoter, GPD promoter, and ADH promoter may, each respectively, have nucleotide sequences of SEQ ID NOS: 13, 14, 15, 16, 17, and 18. The terminator may be selected from the group consisting of phosphoglycerate kinase 1 (PGK1), cytochrome c transcription (CYC1), and GAL1. The CYC1 terminator may have a nucleotide sequence of SEQ ID NO: 19. The vector may further include a selection marker. The selection marker may be ura3 (an orotidine-5'-phosphate decarboxylase).

According to another aspect of the present invention, provided is a method of preparing a lactate dehydrogenase mutant having catalytic activity for conversion of pyruvate into lactate. The preparation method includes a process for mutating (substituting or otherwise changing) one or more amino acid residues to shorten the distance between pyruvate and a catalytic site of the lactate dehydrogenase. Alternatively or in addition, the preparation method may include mutating at least one amino acid residue to increase pKa of a proton donor residue of a catalytic site of the lactate dehydrogenase. The amino acid residue may be as described above.

According to another aspect of the present invention, provided is a cell including a polynucleotide coding for a lactate dehydrogenase having catalytic activity for conversion of pyruvate into lactate (i.e., a recombinant cell).

The polynucleotide encoding a lacatate dehydrogenase that converts pyruvate to lactate is the same as defined above in the specification. The polynucleotide encoding a lacatate dehydrogenase may be an exogenous gene. The yeast cell may include an expression cassette or a vector including the exogenous gene. For example, the yeast cell may include an exogenous gene that is introduced into a parent cell through an expression vector. The yeast cell may include an exogenous gene that is introduced into a parent cell in the form of a linear polynucleotide, for example, as an expression cassette. The exogenous gene may be expressed from an expression vector, for example, a plasmid, in a cell. Also, the exogenous gene may be expressed by being inserted to a genetic material, for example, chromosome, in a cell for its stable expression.

The yeast cell may express the lactate dehydrogenase described above. The yeast cell may have an increased activity of converting pyruvate into lactate compared to that of a parent cell.

As used herein, the term "a parent cell" denotes an original cell, for example, a cell that is not genetically engineered with respect to the same type of a yeast cell that is genetically engineered. In terms of a specific genetic modification, the "parent cell" is a cell with the same characteristics of the genetically engineered one, except that the specific genetic modification is not occurred in the parent cell. Thus, the parent cell may be a cell that is used as a starting material for producing a yeast cell, which has an increased activity of a given protein (e.g., a protein having a sequence identity of about 95% or more with an enzyme that catalyzes conversion of pyruvate into lactate) and is genetically engineered.

As used herein, the term "increase in activity" or "increased activity" may refer to a detectable increase in an activity of a cell, a protein, or an enzyme. The "increase in activity" or "increased activity" may refer to a modified activity of a cell, a protein, or an enzyme which is modified into a higher level (e.g., genetically modified) than those of a comparable cell, protein, or enzyme of the same type, where the comparable cell, protein, or enzyme is a cell, protein, or enzyme that is not genetically modified (e.g., an original or wild-type cell, protein, or enzyme). The term "a cell activity" may refer to an activity of a specific protein or enzyme of a cell. For example, an activity of the modified or engineered cell, protein, or enzyme may be about 5% or more, about 10% or more, about 15% or more, about 20% or more, about 30% or more, about 50% or more, about 60% or more, about 70% or more, or about 100% or more increased than that of an unmodified cell, protein, or enzyme, for example, a wild-type cell, protein, or enzyme, of the same type. An activity of a specific protein or enzyme in a cell may be, for example, about 5% or more, about 10% or more, about 15% or more, about 20% or more, about 30% or more, about 50% or more, about 60% or more, about 70% or more, or about 100% or more increased than an activity of the same protein or enzyme in an unmodifed cell. The cell having an increased activity of a protein or enzyme may be confirmed by using a method known in the art. The cell having an increased activity may have genetic modification that increases an activity of at least one enzyme or polypeptide compared to that of a cell that not genetically modified.

The cell may be a yeast cell, for example, a type of ascomycota. The ascomycota may be saccharomycetaceae. The saccharomycetaceae may be *Saccharomyces* genus, *Kluyveromyces* genus, *Candida* genus, *Pichia* genus, *Issatchenkia* genus, *Debaryomyces* genus, *Zygosaccharomyces* genus, or *Saccharomycopsis* genus.

The *Saccharomyces* genus may be, for example, *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum*, or *S. zonatus*. The *Kluyveromyces* genus may be *Kluyveromyces thermotolerans*. The *Candida* genus may be *Candida glabrata*. The *Zygosaccharomyces* genus may be *Zygosaccharomyces bailli* or *Zygosaccharomyces rouxii.*

The yeast cell may include a non-natural yeast cell. The expression, "non-natural" may include a wild-type strain of a standard strain, in which the non-natural may have one or more genetic modifications that are not generally found in a natural strain of the standard strain. The one or more genetic modifications include insertion of a polynucleotide coding for a polypeptide, addition of other polynucleotides, deletion of a polynucleotide and/or destruction of other functions of genetic materials of the yeast cell. Such modifications include, for example, modifications of a coding region with respect to heterologous, homologous, or both heterologous and homologous polypeptides and a functional fragment thereof. Additional modifications include modifications of, for example, a non-coding regulatory sequence that modifies an expression of a gene or an operon. For example, the yeast cell may include an exogenous gene encoding the enzyme so as to have an activity of converting pyruvate into lactate, have genetic modification increasing activity of a pathway that accelerates or assists flow of metabolites to lactate, and/or have genetic modification decreasing an activity of a pathway that disturbs flow of metabolites to lactate.

Examples of a metabolic polypeptide include enzymes or proteins in a biosynthetic pathway with respect to lactate, in which the biosynthetic pathway includes lactate. Accordingly, a non-natural yeast cell may include genetic modifications with respect to a nucleic acid coding for a metabolic polypeptide or a functional fragment thereof.

The yeast cell may express the lactate dehydrogenase mutant. The yeast cell may have increased conversion activity of pyruvate into lactate due to the expression of a lactate dehydrogenase mutant. The parent strain may be a strain that is the origin of the yeast cell. The yeast cell may have lactate productivity. The catalytic activity of conversion of pyruvate into lactate may increase sufficiently to produce lactate. The catalytic activity may be increased such that the lactate productivity may be about 5.0% or greater, about 5.5% or greater, about 6.0% or greater, about 6.5% or greater, about 7.0% or greater, about 7.5% or greater, about 8.0% or greater, about 8.5% or greater, about 9.0% or greater, about 9.5% or greater, about 10.0% or greater, about 10.5% or greater, about 11.0% or greater, about 11.5% or greater, about 12.0% or greater, about 12.5% or greater, about 13.0% or greater, about 13.5% or greater, about 14.0% or greater, about 14.5% or greater, about 15.0% or greater, about 15.5% or greater, about 16.0% or greater, or about 16.5% or greater than the lactate productivity of the control yeast cell that does not express a lactate dehydrogenase mutant (i.e., an unmodified yeast cell).

The yeast cell may have a reduced activity of a pathway that disturbs flow of metabolites to lactate compared to that of the parent cell. As used herein, the term "decrease in activity" or "decreased activity" refers to a cell having an activity of an enzyme or polypeptide at a level lower than that measured in the parent cell (e.g., a genetically unengineered cell). Also, the term "decreased in activity" or "decreased activity" refers to an isolated enzyme or polypeptide having an activity level that is lower than that of an original or wild-type enzyme or polypeptide. The "decrease in activity" or "decreased activity" includes no activity. For example, an enzyme conversion activity from a substrate to a product with respect to a modified (e.g., genetically engineered) cell or enzyme may be about 20% or more, about 30% or more, about 40% or more, about 50% or more, about 55% or more, about 60% or more, about 70% or more, about 75% or more, about 80% or more, about 85% or more, about 90% or more, about 95% or more, or about 100% decreased, compared to an enzyme conversion activity of a cell or an enzyme of a cell or enzyme that is not modified, for example, the parent cell or the "wild-type" cell. The decreased activity of the enzyme or cell may be confirmed by using a method known in the art. The decreased activity includes a case when an enzyme has no activity or a decreased activity compared to that of a cell without genetic modification, for example, the parent cell or wild-type cell, in spite of the expression of the enzyme, a gene that encodes the enzyme is not expressed or an expressed amount is decreased compared to that of an originally unengineered gene even when the gene is expressed. The cell having a decreased activity may have genetic modification that decreases an activity of at least one enzyme or polypeptide compared to that of a cell that does not have genetic modification.

The decrease in an activity of the enzyme may be caused by deletion or disruption of a gene encoding the enzyme. The "deletion" or "disruption" of the gene refers to a case when a part of or the whole gene or a part of or the whole of a regulatory factor such as its promoter or its terminator region is modified, substituted, or deleted, or when at least one base is inserted to the gene so that the gene is not expressed, an expressed amount is reduced, or an enzyme activity is not observed or reduced even when the gene is expressed. The deletion or disruption of the gene may be achieved by genetical engineering such as homologous recombination, generation of mutation, or molecular evolution. When a cell includes a plurality of the same genes or at least two different polypeptide paralogous genes, one or more of the genes may be deleted or disrupted.

The yeast cell may have a decrease activity of a polypeptide converting pyruvate into acetaldehyde, a polypeptide converting lactate into pyruvate, or a combination thereof, compared to that of the parent cell.

When the yeast cell is for production of lactate, the yeast cell may have a decreased activity of polypeptide converting pyruvate into acetaldehyde. The polypeptide that converts pyruvate into acetaldehyde may be an enzyme classified as EC 4.1.1.1. The polypeptide that converts pyruvate into acetaldehyde may have an amino acid sequence having about 75% or more, 80% or more, 90% or more, 95% or more, 96% or more, 97% or more, 98% or more, 99% or more, or 100% of sequence identity with an amino acid sequence of SEQ ID NO: 9. A gene coding for the polypeptide that converts pyruvate into acetaldehyde may have a polynucleotide sequence having about 75% or more, 80% or more, 85% or more, 90% or more, 95% or more, 96% or more, 97% or more, 98% or more, 99% or more, or 100% of sequence identity with an polynucleotide sequence of SEQ ID NO: 11. The gene may be a pdc1, pdc2, pdc5, or pdc6 coding for a pyruvate decarboxylase (PDC).

The yeast cell may have a decreased activity of polypeptide converting lactate into pyruvate. The polypeptide converting lactate into pyruvate may be a cytochrome c-dependent enzyme. The polypeptide converting lactate into pyruvate may be a cytochrome-c oxidoreductase (CYB2). The lactate CYB2 may be an enzyme that is classified under EC 1.1.2.4 acting on D-lactate or EC 1.1.2.3 acting on L-lactate. The polypeptide converting lactate into pyruvate may have a sequence identity of about 75% or more, about 80% or more, about 85% or more, about 90% or more, about 95% or more, about 96% or more, about 97% or more, about 98% or more, about 99% or more, about 100% with an amino acidsequence of SEQ ID NO: 10. A gene that encodes the polypeptide converting lactate into pyruvate may have a sequence identity of about 75% or more, about 80% or more, about 85% or more, about 90% or more, about 95% or more, about 96% or more, about 97% or more, about 98% or more, about 99% or more, about 100% with a nucleotide sequence encoding an amino acid sequence of SEQ ID NO: 10. The cyb2gene may have a nucleotide sequence of SEQ ID NO: 12.

According to another aspect of the present invention, provided is a method of producing lactate, the method including culturing the yeast cell in a cell culture medium, whereby the yeast cell produces lactate, and retrieving lactate from cultured products obtained therefrom.

The terms "culturing", "fermentation", and "production through fermentation" are interchangeably used and these terms indicate growth of a strain in a suitable growth culture medium including a carbon source, which is used for the growth of the strain and/or production of lactate, which is a desired product. The suitable medium is a medium suitable for culturing and growth of the strain. Such a medium is known in the field of strain fermentation according to a strain to be cultured. The suitable medium includes a supply source of carbon, which may be any carbon supply source that may be metabolized by the strain. The metabolism refers to a conversion of energy and material that enables growth of the strain or enables the strain to maintain its life.

In the culturing, the cell may be cultured in a batch, fed-batch, or continuous manner. The culturing may be performed in a medium containing a carbon source, for example, a medium including glucose. The medium used in culturing the yeast cell may be any general medium suitable for growth of a host cell, such as a minimum or composite medium including suitable supplements. The suitable medium may be obtained from a commercial seller or prepared according to a known preparation method.

The medium used in the culturing may be a medium that may satisfy requirements of a specific yeast cell. The medium may be a medium selected from the group consisting of a carbonaceous source, a nitrogen source, a salt, a trace element, and a combination thereof.

To obtain lactate from the genetically manipulated yeast cell, culture conditions may be suitably adjusted. The cell may be cultured in an aerobic condition for proliferation of the cell. Thereafter, to produce lactate, the cell may be cultured under anaerobic conditions. The anaerobic conditions denotes environments having no oxygen. As used herein, the microaerobic conditions, when used in reference to a culture or growth condition, refers that a dissolved oxygen (DO) concentration in a medium remains between about 0% and about 10% of saturation for dissolved oxygen in liquid media Microaerobic conditions also include growing or resting cells in liquid medium or on a solid agar plate inside a sealed chamber maintained with an atmosphere of less than 1% of oxygen. The concentration of oxygen can be maintained by, for example, sparging the culture with an $N_2/CO_2$ mixture or other suitable non-oxygen gas. The oxygen conditions may include maintaining a dissolved oxygen (DO) concentration of 0% to 10%, for example, 0% to 8%, 0% to 6%, 0% to 4%, or 0% to 2%. The term "culture condition" indicates a condition for culturing a yeast cell. Such a culture condition may include for example, a carbon source, a nitrogen source, or an oxygen condition for the yeast cell to use. The carbon source used by the yeast cell may include monosaccharides, disaccharides, or polysaccharides. For example, the carbon source may include glucose, fructose, mannose, or galactose. The nitrogen source used by the yeast cell may include an organic nitrogen compound or an inorganic nitrogen compound. For example, the nitrogen source may include an amino acid, amide, amine, a nitrate, or an ammonium salt. A metabolic pathway may be modified in accordance with the carbon source or the nitrogen source that may be used by the yeast cell.

The obtaining of the lactate from the cultured product may be performed by using a method known in the art. The separation method may be centrifugation, filtration, ion-exchange chromatography, or crystallization. For example, the cultured product may be centrifuged at a low rate to remove a biomass, and the supernatant resulting therefrom may be separated through ion-exchange chromatography.

Example 1

Preparation of a Lactate Dehydrogenase (L-LDH) Expression Vector for Production of Lactate 1.1 Preparation of Mutant of Gene Encoding Lactate Dehydrogenase and Preparation of Vector Including the Mutant In order to clone a CCW12p promoter of a CCW12 gene known as to induce gene expression in *Saccharomyces cerevisiae*, PCR was performed with a genomic DNA of *Saccharomyces cerevisiae* (CEN.PK2-1D, genotype: MATα ura3-52; trp1-289; leu2-3,112; his3△1; MAL2-8C; SUC2, EUROSCARF accession number: 30000B) as a template and using a primer set of SEQ ID NOS: 20 and 21 as primers, the PCR fragment thus obtained was digested with SacI and XbaI, and then resultant was inserted into pRS416 vector (ATCC® 7521™), producing a pRS416-CCW12p vector. FIG. 1 is an illustration of the pRS416 vector. The pRS416 vector is a yeast centromere shuttle plasmid that has a T7 promoter, an ampicillin resistance in bacteria, a URA3 cassette (a selection marker) in a yeast, and a restriction enzyme cloning site.

A wild-type lactate dehydrogenase gene ($BtLDH_w$) of SEQ ID NO: 2 was amplified by performing PCR using gDNA of *Bos Taurus* as a template and a primer set of SEQ ID NOS: 22 and 23 as primers. Side direct mutagenesis was performed using the wild-type lactate dehydrogenase gene thus obtained as a template to obtain a gene ($BtLDH_w$) that encodes a lactate dehydrogenase mutant. Genes encoding the mutant, each respectively, have polynucleotide sequences of SEQ ID NOS: 6 to 8. The lactate dehydrogenase mutant is shown in Table 1.

The genes encoding the lactate dehydrogenase mutant, which are Idh(E102G), Idh(D236G), and Idh(S237G) genes, were each introduced to the pRS416-CCW12p vector by using a restriction enzyme BamHI/HindIII to produce a pRS416-CCW12p-$BtLDH_M$ vector.

TABLE 1

| | Lactate dehydrogenase mutant derived from *Bos Taurus* ($ldh_M$) | Mutation | SEQ ID NO of amino acid | SEQ ID NO of gene |
|---|---|---|---|---|
| 1 | BtLDH(E102G) | E102G | 3 | 6 |
| 2 | BtLDH(D236G) | D236G | 4 | 7 |
| 3 | BtLDH(S237G) | S237G | 5 | 8 |

1.2 Preparation of Lactate Dehydrogenase (L-LDH) Expression Vector for Production of Lactate (1.2.1) Selection of Lactate Dehydrogenase Mutants Through Homology Modeling (1) Prediction of Yeast Structure A structure of a *Bos Taurus* derived lactate dehydrogenase (BtLDH) was predicted by homology modeling using Discovery studio 3.5 software (Accelrys Inc.). The homology modeling is a method of predicting the structure of a novel protein based on a structure of a template protein, a structure of which is already known. Herein, a structure of *Squalus acanthias* derived L-LDH (PDB database ID: 3LDH, Mol. Biol. 102 (1976): 759-779) was used as a template to predict a structure of a wild-type BtLDH. As a result, a predicted structure of the wild-type BtLDH was energy minimized by using Discovery Studio 3.5 to predict a more stable structure of the wild-type BtLDH. The structure of the wild-type BtLDH was used to predict a structure of a BtLDH mutant by using a "build mutant" option in the Discovery Studio 3.5, and the structure of the BtLDH mutant was energy minimized in the same manner as described above to predict a more stable structure thereof. The 108th position residue of the wild-type BtLDH was changed to a different amino acid to produce 19 mutants. Table 1 shows BtLDH mutants.

(2) Measuring a Distance Between a Catalytic Site of a Lactate Dehydrogenase Mutant and Pyruvate Among the predicted structures of the lactate dehydrogenase mutants, distances between pyruvate, which is a ligand of the lactate dehydrogenase, and each of 106th position, 193rd position, and 169th position residues in a catalytic site of the mutant were measured. Table 2 shows distances between pyruvate and residues in catalytic sites of the BtLDH mutant. The closer the pyruvate is to the residue compared with that of the wild-type lactate dehydrogenase, the stronger the bond between the pyruvate and the lactate dehydrogenase, which is advantageous for the conversion of pyruvate into lactate by the lactate dehydrogenase mutant. As shown in Table 2, in the case of lactate dehydrogenase mutants such as Asn108Gly, Asn108Leu, Asn108Arg, and Asn108Met, a distance between pyruvate and a 106th position Arg residue of the mutant (d106), a distance between pyruvate and a 193rd position His residue of the mutant (d193), and a distance between pyruvate and a 169th position Arg residue of the mutant (d169) were all closer than those of the wild-type lactate dehydrogenase (each of which was 6.48 Å, 5.04 Å, and 4.49 Å).

(3) Prediction of pKa of His193 in the Lactate Dehydrogenase Mutant

Among the mutant structures and the wild-type structures shown in Table 2, pKa of His193 that acts as a proton donor in an active site was predicted by using Discovery Studio 3.5 software (Accelrys Inc.). When pKa of His193 increases, protons may be emitted more thoroughly and thus, conversion from pyruvate into lactate by the lactate dehydrogenase mutant may occur easily. As shown in Table 2), in lactate dehydrogenase mutants, Asn108Gly, Asn108Leu, Asn108Ala, Asn108Asp, Asn108Gln, Asn108Glu, Asn108His, Asn108Phe, Asn108Ser, Asn108Trp, and Asn108Tyr, pKa of His193 in the lactate dehydrogenase mutants was higher than the pKa of His193 in a wild-type lactate dehydrogenase.

From the results shown in Examples 1.2.1, it may be concluded that a catalytic site of the lactate dehydrogenase mutant and pyruvate are close to each other and that the mutant having a high pKa of His193 has the 108th position residue of the mutant substituted to Gly or Leu.

TABLE 2

| Distance between Pyr and Asn108 mutant | d106 (Å) | d193 (Å) | d169 (Å) | pKa of His193 |
|---|---|---|---|---|
| Asn(W/T) | 6.48 | 5.04 | 4.49 | 5.93 |
| Ala | 6.08 | 4.17 | 4.71 | 5.99 |
| Arg | 6.42 | 4.27 | 4.48 | 5.73 |
| Asp | 6.32 | 4.28 | 4.54 | 6.09 |
| Cys | 6.52 | 4.26 | 4.36 | 5.86 |
| Gln | 6.26 | 4.31 | 4.54 | 5.97 |
| Glu | 6.25 | 4.25 | 4.56 | 6.46 |
| Gly | 6.42 | 4.31 | 4.43 | 6.07 |
| His | 6.40 | 4.25 | 4.49 | 6.00 |
| Ile | 6.32 | 4.21 | 4.51 | 5.79 |
| Leu | 6.41 | 4.26 | 4.47 | 6.15 |
| Lys | 6.68 | 4.24 | 4.45 | 5.89 |
| Met | 6.41 | 4.22 | 4.41 | 5.81 |
| Phe | 6.11 | 4.22 | 4.72 | 5.96 |
| Pro | 6.11 | 4.22 | 4.70 | 5.49 |
| Ser | 6.57 | 4.22 | 4.45 | 6.04 |
| Thr | 6.01 | 4.22 | 4.93 | 5.92 |
| Trp | 6.37 | 4.21 | 4.52 | 6.10 |
| Tyr | 6.45 | 4.29 | 4.57 | 6.15 |
| Val | 6.63 | 4.24 | 4.34 | 5.86 |

(1.2.2) Preparation of Lactate Dehydrogenase (L-LDH) Expression Vector for Production of Lactate A cassette for inserting a wild-type lactate dehydrogenase or a lactate dehydrogenase (L-LDH) mutant was prepared as follows. To clone a promoter region (CCW12p) of a CCW12 gene, which is known to induce gene expression in *Saccharomyces cerevisiae*, genomic DNA *Saccharomyces cerevisiae* (CEN.PK2-1D, gene type: MATα ura3-52; trp1-289; leu2-3,112; his3△1; MAL2-8$^{C}$; SUC2, EU$^{R}$OSCARF accession number: 30000B) was used as a template, primers of SEQ ID NO: 58 and 59 were used to perform PCR (performed at a temperature of 98° C. for 5 minutes, 30 times repeated at a temperature of 98° C. for 30 seconds, at a temperature of 55° C. for 30 seconds, at a temperature of 72° C. for 1 minute, and then at a temperature 72° C. for 1 minute, PCR fragments obtained therefrom were excised by using SacI and XbaI, and products obtained therefrom were inserted into a pRS416 vector (ATCC®87521™) to prepare pRS416-CCW12p. FIG. 1 shows a pRS416 vector.

gDNA of *Bos Taurus* was used as a template, and primers of SEQ ID NO: 60 and 61 were used to perform PCR and amplify wild-type lactate dehydrogenase gene of SEQ ID NO: 2. The gene coding for the wild-type lactate dehydrogenase obtained therefrom was excised by using an EcoR1/SalI restriction enzyme to insert the fragments obtained therefrom into pRS416-CCW12p, to thereby prepare pRS416-CCW12p-BtLDH$_{wt}$. Additionally, the wild-type lactate dehydrogenase gene obtained therefrom was used as a template to perform site directed mutagenesis, to thereby obtain genes (Btldh$_{M}$), each coding for lactate dehydrogenase mutants BtLDH(N108G) and BtLDH(N108L). The mutant gene is SEQ ID NO: 5 or 6. The genes coding for the mutants were excised by using the EcoR1/SalI restriction enzyme, and fragments obtained therefrom were inserted into pRS416-CCW12p, thereby producing pRS416-CCW12p-BtLDH(N108G) and pRS416-CCW12p-BtLDH (N108L), respectively.

Example 2

Preparation of *S. cerevisiae* Including Lactate Dehydrogenase Mutant 2.1 Preparation of *S. cerevisiae* CEN.PK2-1D (Δ Pdc1+BtLD$_{HM}$)

2.1.1 Preparation of a PDC1 Gene Deletion Cassette

To delete a pyruvate decarboxylase 1 (PDC1), which participates in the production of ethanol from pyruvate, through a homologous recombination method, a gene deletion vector was prepared as follows.

To use an antibiotic marker, genomic DNA of *S. cerevisiae* (CEN.PK2-1D) was used as a template and primers of SEQ ID NO: 24 and 25 were used to prepare a PCR fragment of Gal10 terminator (Gal10t), which was then excised by using NotI, and fragments obtained therefrom were inserted into pGEM-5Zf (Promega USA) to prepare pGEM-Gal10t.

Figure 2:
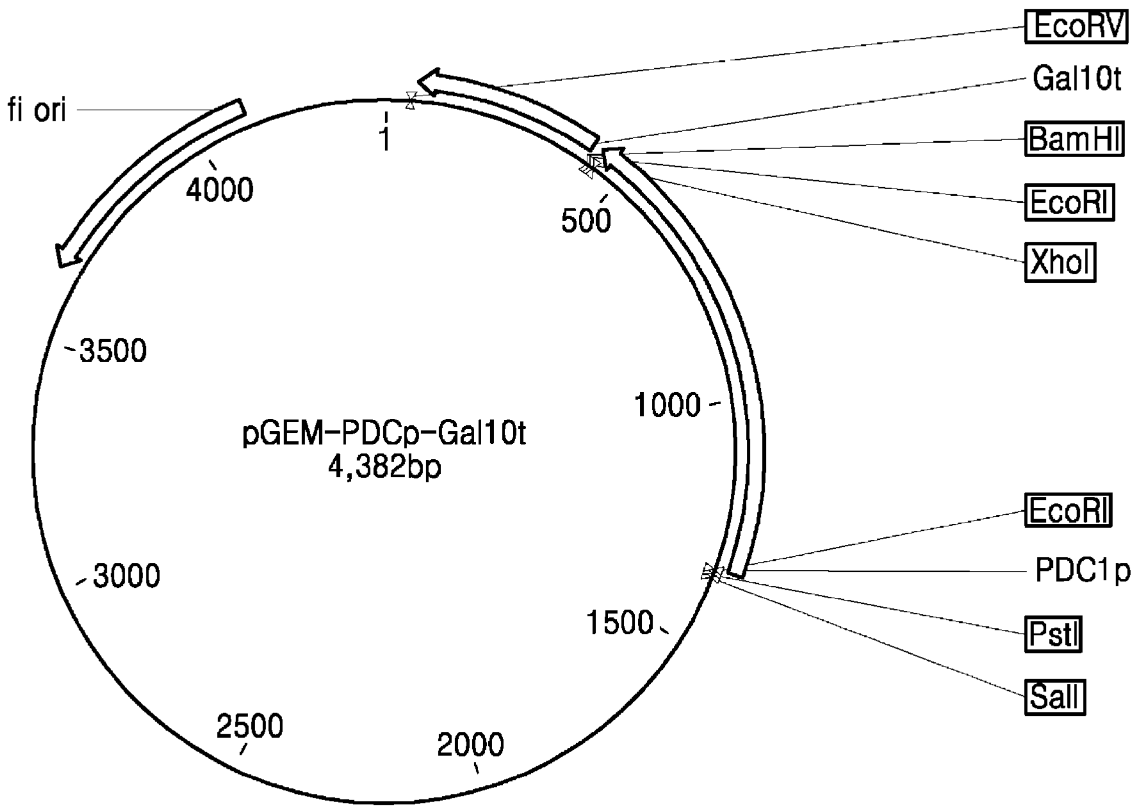
FIG. 2 is an illustration of a pGEM-PDCp-Gal10t vector.

Also, PCR was performed with a genomic DNA of *S. cerevisiae*, CEN.PK2-1D as a template and a primer set of SEQ ID NOS: 26 and 27 as primers to obtain a PDC promoter (PDCp), a fragment thus obtained was digested with EcoRI, and the resultant was ligated to a pGEM-Gal10t vector digested with the same EcoRI, producing a pGEM-PDCp-Gal10t vector. FIG. 2 is an illustration of the pGEM-PDCp-Gal10t vector. A pGEM-PDCp-Gal10t vector was prepared through insertion of NTP, which is a geneticin resistance gene, to over-express NTP.

Figure 3:
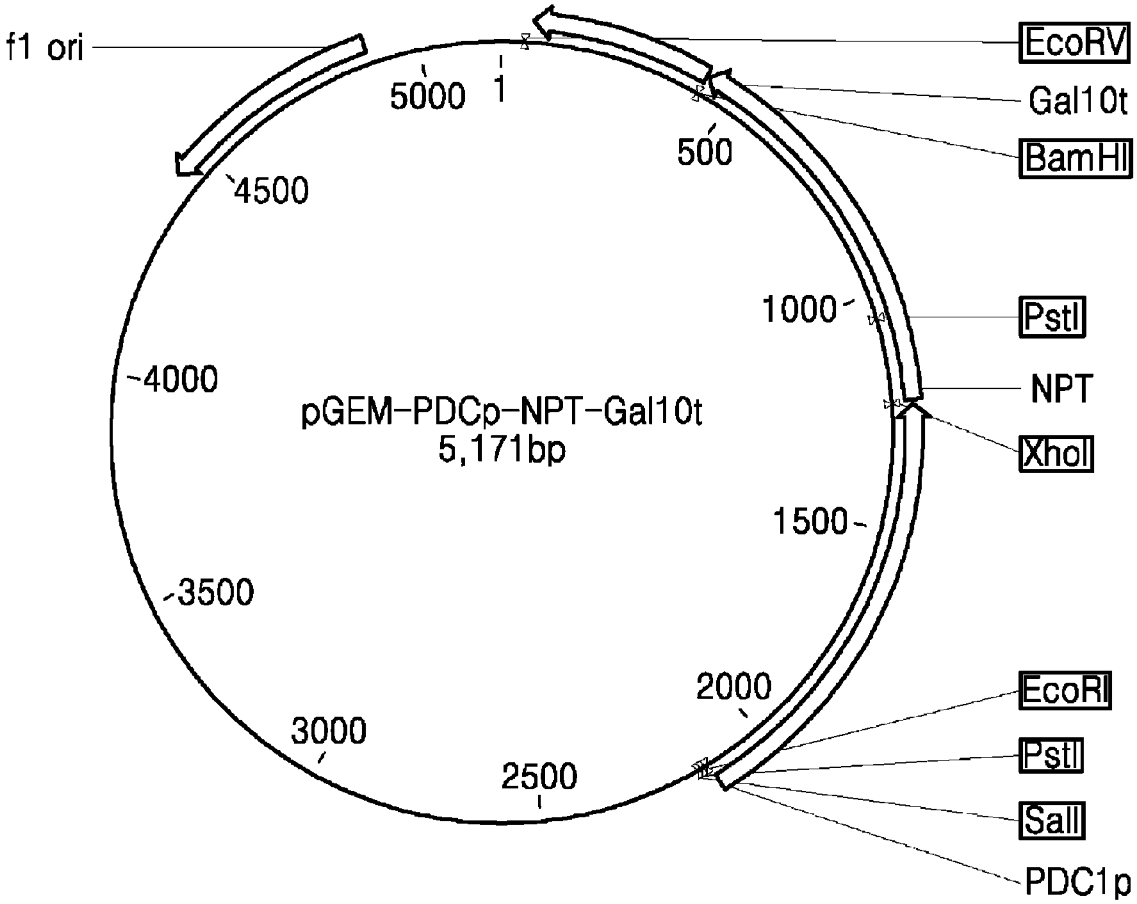
FIG. 3 is an illustration of a pGEM-PDCp-NPT-Gal10t vector, which isan NPT over-expression vector used as a template for preparing a PDC1 deletion cassette.

Then, PCR was performed with pcDNA3.3-TOPO (Invitrogen Co.) as a template and a primer set of SEQ ID NOS: 28 and 29 as primers to obtain a neomycin phosphotransferase (NPT) gene that may enable having tolerance to geneticin (G418) antibiotics, a fragment thus obtained was digested with XhoI and BamHI, and the resultant was ligated to the pGEM-PDCp-Gal10t vector digested with the same restriction enzymes, producing a pGEM-PDCp-NPT-Gal10t vector. FIG. 3 is an illustration of the pGEM-PDCp-NPT-Gal10t vector. The pGEM-PDCp-NPT-Gal10t vector is an NPT over-expression vector, which was used as a template for preparing a PDC1 deletion cassette.

To prepare a PDC1 gene deletion cassette, pGEM-PDCp-NPT-Gal10t was used as a template, and primers of SEQ ID NO: 30 and 31 were used to perform PCR, to thereby prepare a PDC1 gene deletion cassette.

2.1.2 Preparation of *S. cerevisiae* CEN.PK2-1D (△ pdc1) Strain

Figure 4:
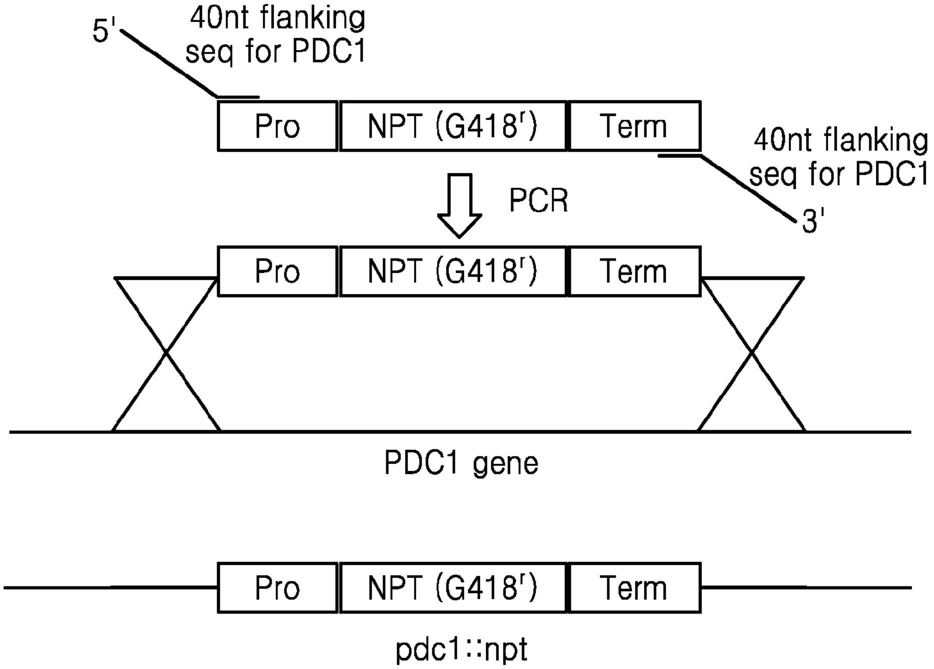
FIG. 4 is a schematic illustration of a process for preparing a mutant strain in which PDC1 is deleted from a parent strain, *S. cerevisiae* CEN.PK2-1D.
Figure 5:
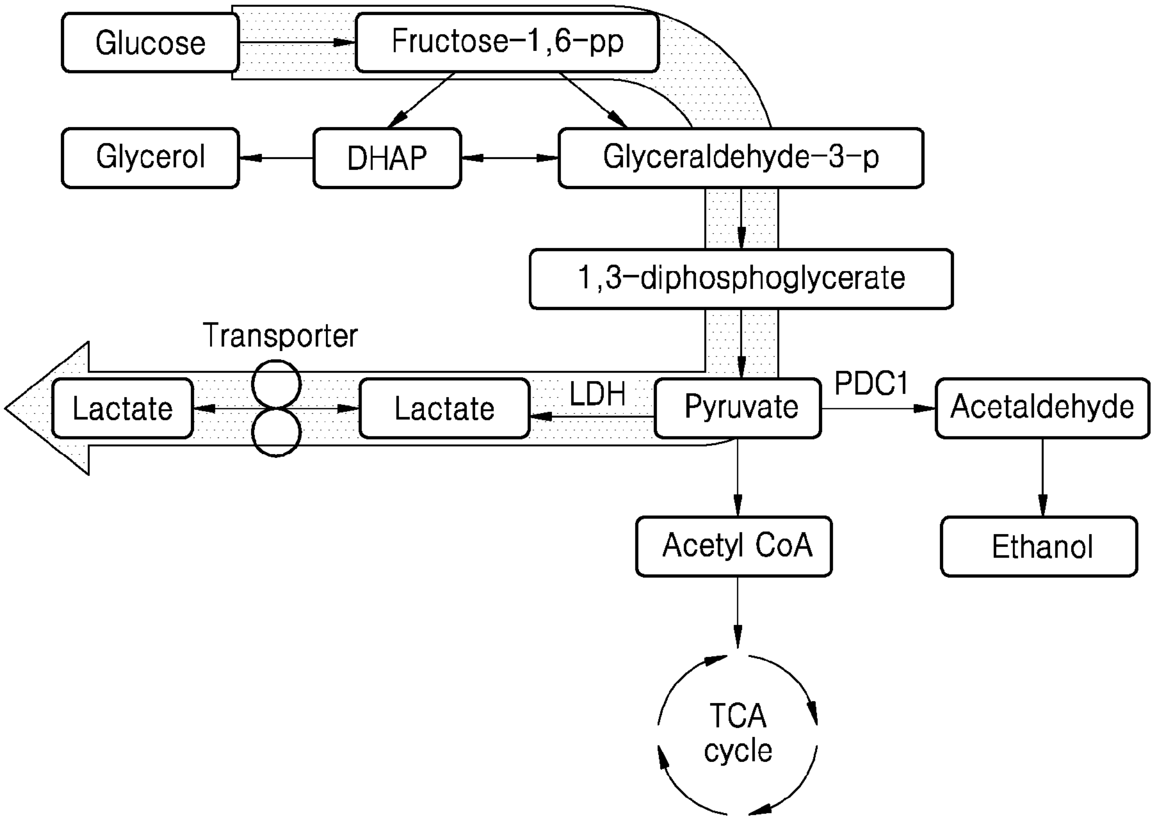
FIG. 5 is an illustration of a pathway for producing lactate from yeast cell.

A mutant strain of *S. cerevisiae* deleted of PDC1 was prepared as follows. FIG. 4 shows processes for preparing a mutant strain in which PDC1 is deleted from a parent strain, *S. cerevisiae* CEN.PK2-1D. The *S. cerevisiae* strain of CEN.PK2-1D was spreaded onto a YPD solid medium (10 g of yeast extract, 20 g of peptone, and 20 g of glucose), cultured for 24 hours at a temperature of about 30° C., and a colony obtained therefrom was inoculated in about 10 ml of YPD liquid medium to culture the same for 18 hours at a temperature of 30° C. A sufficiently grown culture medium was inoculated in about 50 ml of YPD liquid medium in a 250 ml flask at 1%(v/v) to culture the same in an incubator at 230 rpm and at about 30° C. After about 4 to 5 hours, when $OD_{600}$ reached about 0.5, the culture medium was centrifuged at about 4,500 rpm for about 10 minutes to obtain *S. cerevisiae* cells, which were re-suspended in a lithium acetate solution having a concentration of about 100 mM. Thereafter, the cells that were re-suspended at about 4,500 rpm for about 10 minutes were re-suspended in a lithium acetate solution having a concentration of about 1 M including about 15% of glycerol, and then the products obtained therefrom were divided into amounts of 100 μl.

For PDC1 deletion, the PDC1 gene deletion cassette prepared in Example 3 was mixed with 50% polyethylene glycol and single stranded carrier DNA, reacted in a water bath at a temperature of about 42° C. for about 1 hour, and then a culture medium obtained therefrom was spreaded onto YPD including about 100 ug/ml of geneticin to culture the same at a temperature of about 30° C. for about 24 hours or more. 8 colonies (mutant strains) formed on the plate were selected to move the same to a YPD solid medium including about 100 ug/ml of geneticin. Simultaneously, the selected colonies were cultured in a liquid medium of the same composition while genomic DNA was separated from the cultured colonies by using a commercial kit (Gentra Puregene Cell kit, Qiagen, USA). Genomic DNA separated from the mutant strains were used as a template and primers of SEQ ID NO: 32 and 33 were used to perform PCR, and PCR products obtained therefrom were electrophoresed to confirm PDC1 deletion. As a result, *S. cerevisiae* of CEN.PK2-1D (△ PDC1) was obtained.

2.1.3 Preparation of Strain from which PDC1 Gene is Deleted and to which *S. cerevisiae* L-LDH Expression Vector is Introduced The pRS416-CCW12p-BtLDH$_w$ vector and the pRS416-CCW12p-BtLDH$_M$ vector (that is, the pRS416-CCW12p-BtLDH(E102G) vector, pRS416-CCW12p-BtLDH (D236G), pRS416-CCW12p-BtLDH(S237G) vector, pRS416-CCW12p-BtLDH(N108G) vector, and pRS416-CCW12p-BtLDH(N108L) vector) were each introduced to a *S. cerevisiae* CEN.PK2-1D (△ PDC1) strain in which PDC1 is deleted as prepared in Example 2.1.2 by heat shock transformation.

Particularly, the pRS416-CCW12p-BtLDH$_w$ vector prepared in Example 1 and the pRS416-CCW12p-BtLDH$_M$ vector were mixed with 50% polyethylene glycol and a single strand carrier DNA, added to a water bath with a culture solution of a *S. cerevisiae* CEN.PK2-1D (△ PDC1) strain, allowed for reaction for 1 hours at 42° C., and the obtained culture solution was spread onto a ura-free YSD agar plate (including 6.7 g/L of yeast nitrogen base without amino acids and 1.4 g/L of amino acid dropout mix (-ura)) and incubated for about 24 hours or more at 30° C. As a result, a BtLDH vector-introduced strain was prepared.

2.2 Preparation of *S. cerevisiae* CEN.PK2-1D (Δ pdc1 Δ cyb2+BtLDH$_M$)

Figure 6:
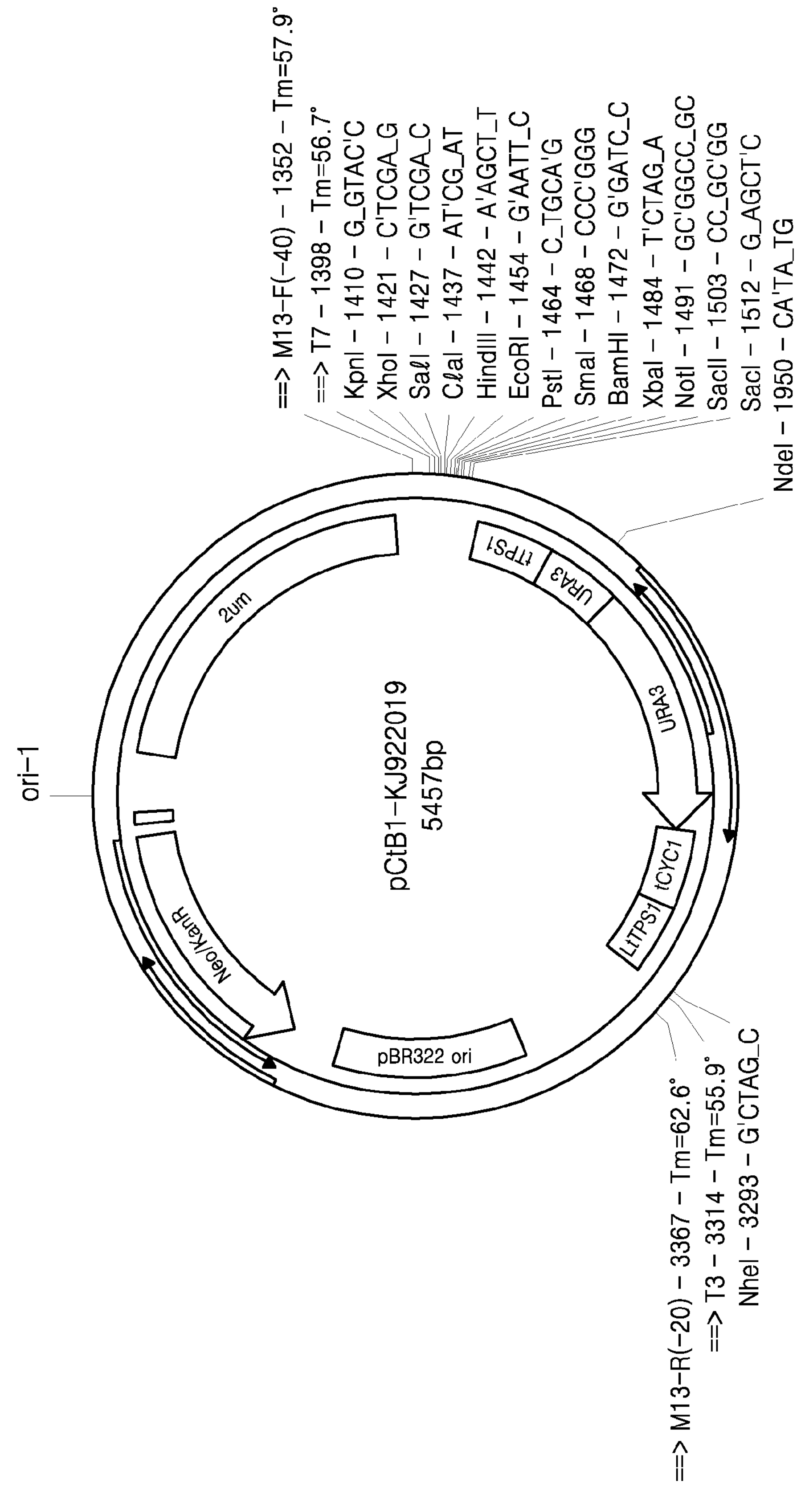
FIG. 6 is a schematic illustration of a pCtB1 vector.

2.2.1 Preparation of L-Lactate Cytochrome-c Oxidoreductase (cyb2) Deletion Strain Preparation of L-Lactate Cytochrome-c Oxidoreductase (cyb2) Deletion Strain PCR with a genomic DNA of a *S. cerevisiae* CEN.PK2-1D wild-type strain as a template and a primer set of SEQ ID NOS: 34 and 35 as primers to obtain a 355 bp DNA fragment. Also, PCR was performed with the same genomic DNA as a template and a primer set of SEQ ID NOS: 36 and 37 as primers to obtain a 378 bp DNA fragment. Also, PCR was performed with the pCtB1 vector (GenBank Accession Number KJ922019; SEQ ID NO: 38) as a template and using a combination of T7 primers and T3 primers to obtain a 1,955 bp DNA fragment. The 355 bp, 378 bp, and 1,955 bp DNA fragments thus obtained were all mixed together, and PCR was performed with a primer set of SEQ ID NOS: 34 and 37 as primers to obtain a 2,630 bp DNA fragment. FIG. 6 is a schematic view of the pCtB1 vector. The DNA fragments thus obtained were transformed to the CEN.PK2-1D strain, and strains grown in a minimal medium free of uracil (SD-URA; including 6.7 g of yeast nitrogen base, 1.92 g of synthetic drop-out without uracil, 20 g of D-glucose, and 20 g/L of Bacto agar) were isolated. On a wild-type strain among the isolated strains, PCR was performed with a primer set of SEQ ID NOS: 39 and 40 in which a 2,676 bp DNA fragment was confirmed as primers to secure a strain in which a 2,891 bp DNA fragment was confirmed.

The secured strain was seed cultured in a YPD agar plate (including 10 g of yeast extract, 20 g of Bacto Peptone, and 20 g/L of D-glucose) for one day, spread on a 5-FOA plate (including 6.7 g of yeast nitrogen base, 1.92 g of synthetic drop-out without uracil, 0.1 g of uracil, 20 g of D-glucose, 1 g of 5-fluoroorotic acid, and 20 g/L of Bacto agar), and strains grown from the medium were isolated. On the isolated strains, PCR was performed with a primer set of SEQ ID NOS: 39 and 40 as primers to secure a strain in which a 1,497 bp DNA fragment was confirmed. The strain was named as a MD1192 strain. A genotype of the MD1192 strain is as follows: MATαura3-52; trp1-289; leu2-3,112; his3Δ1; MAL2-8C; SUC2; Δcyb2.

2.2.2 Preparation of Cassette for Overexpression of L-ldh Gene

Figure 7:
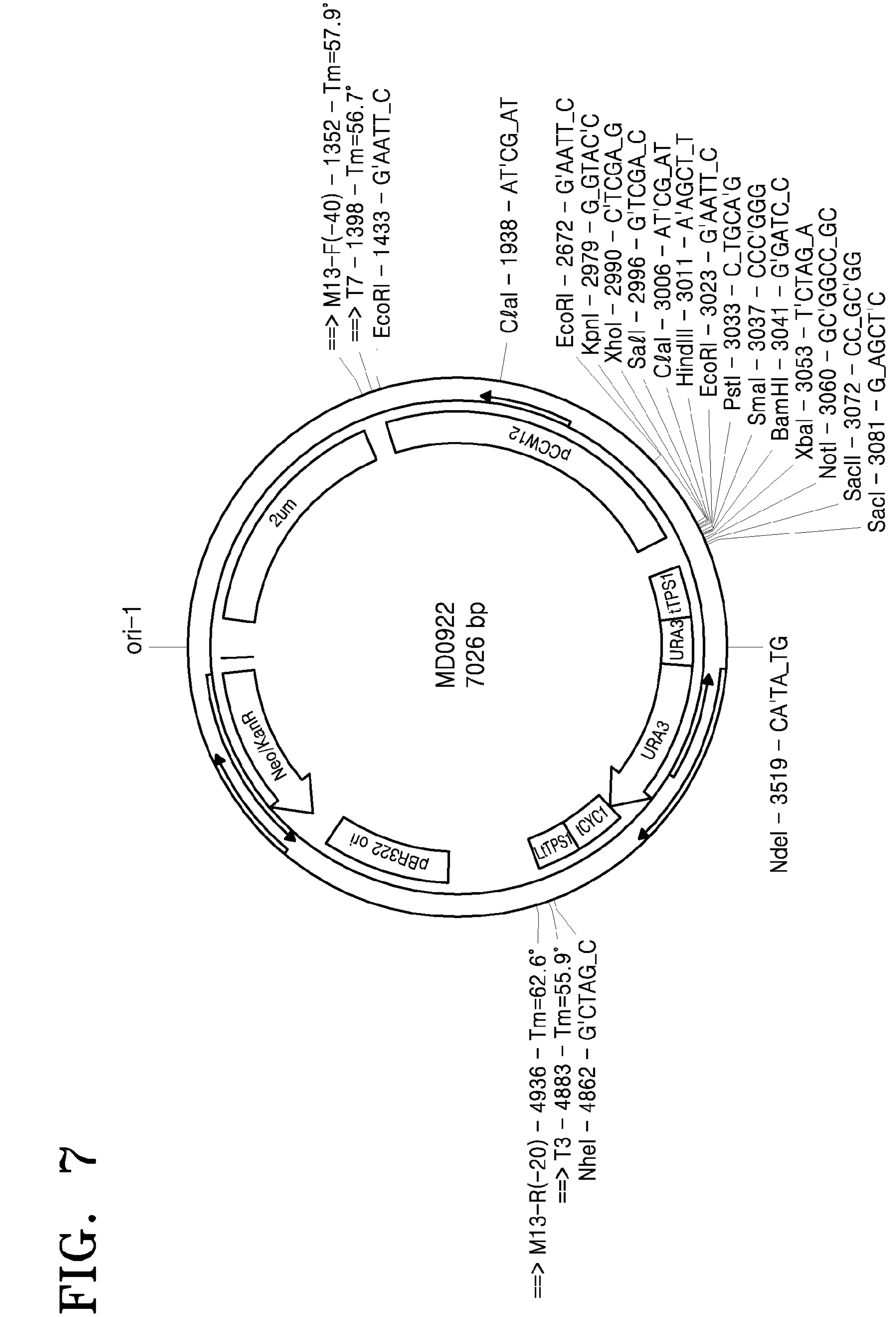
FIG. 7 is a schematic illustration of a MD0922 vector.

In order to prepare a cassette for overexpression of L-LDH by a CCW12 promoter in a *S. cerevisiae* strain, a MD0922 vector was prepared by inserting the CCW12 promoter into the pCtB1 vector. To obtain the CCW12 promoter, PCR was performed with a genomic DNA of a *S. cerevisiae* CEN.PK2-1D natural type strain as a template and a primer set of SEQ ID NOS: 41 and 42 as primers to obtain a 1, 605 bp DNA fragment. The DNA fragment thus obtained was mixed with a pCtB1 vector digested with KpnI, cloned by using an in-fusion kit, introduced to TOP10 (Invitrogen), which is an *E. coli* strain, by using a general heatshock transformation method, and spread on a LB agar plate including 50 ug/ml of kanamycin (including 10 g/L of Bacto Tryptone, 5 g/L of yeast extract, 10 g/l of sodium chloride, 15 g/L of Bacto agar, and 50 ug/ml of kanamycin). Plasmid was collected from the colonies grown for 10 hours at 37° C. collected by using a general alkaline lysis miniprep method, and vectors such as SEQ ID NO: 43 among the plasmid were selected to obtain a MD0922 vector, which is a yeast overexpression vector. FIG. 7 is a schematic view of the MD0922 vector. The MD0922 vector is a vector prepared by inserting a CCW12 promoter to the pCtB1 vector.

Figure 8:
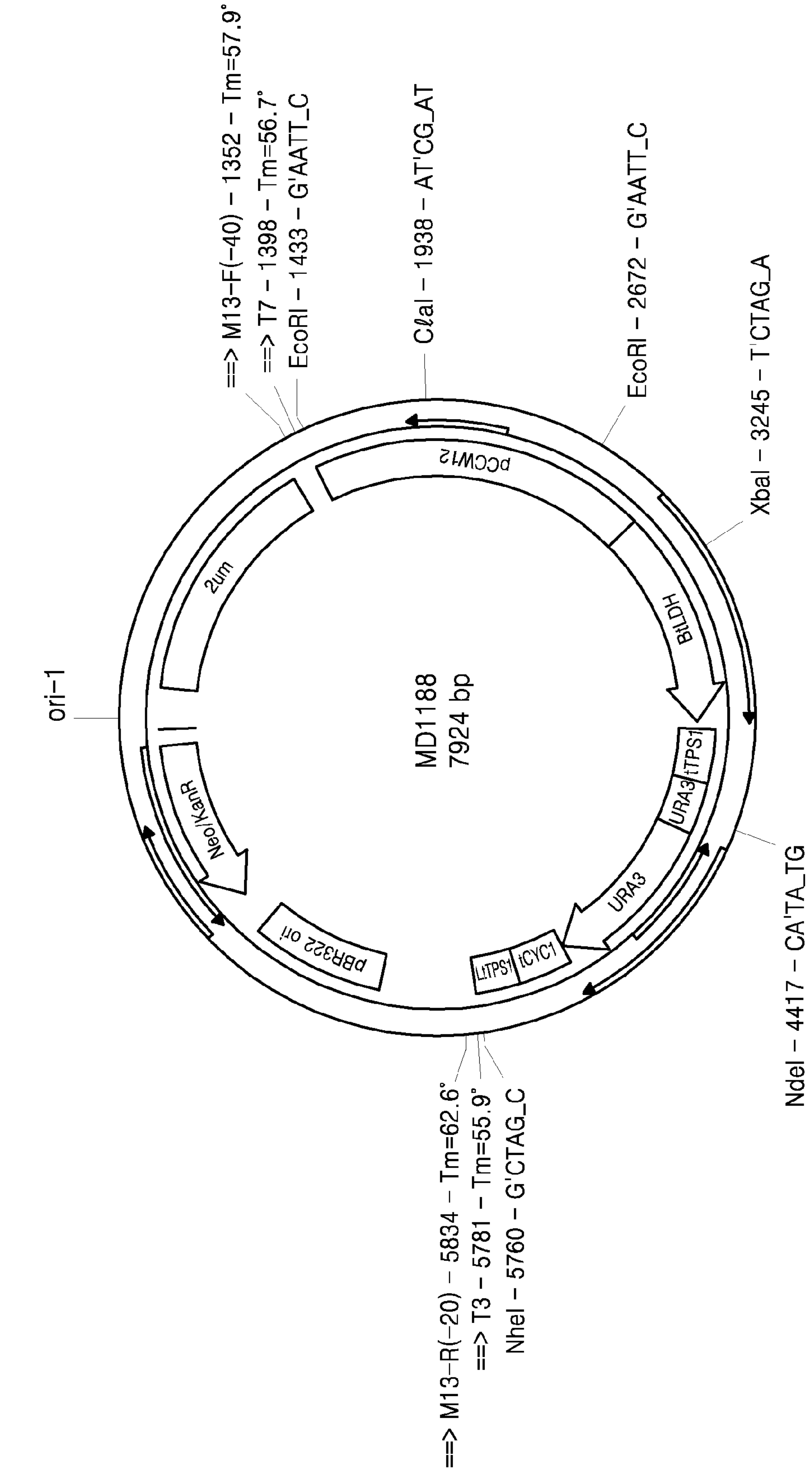
FIG. 8 is a schematic illustration of a MD1188 vector.
Figure 9:
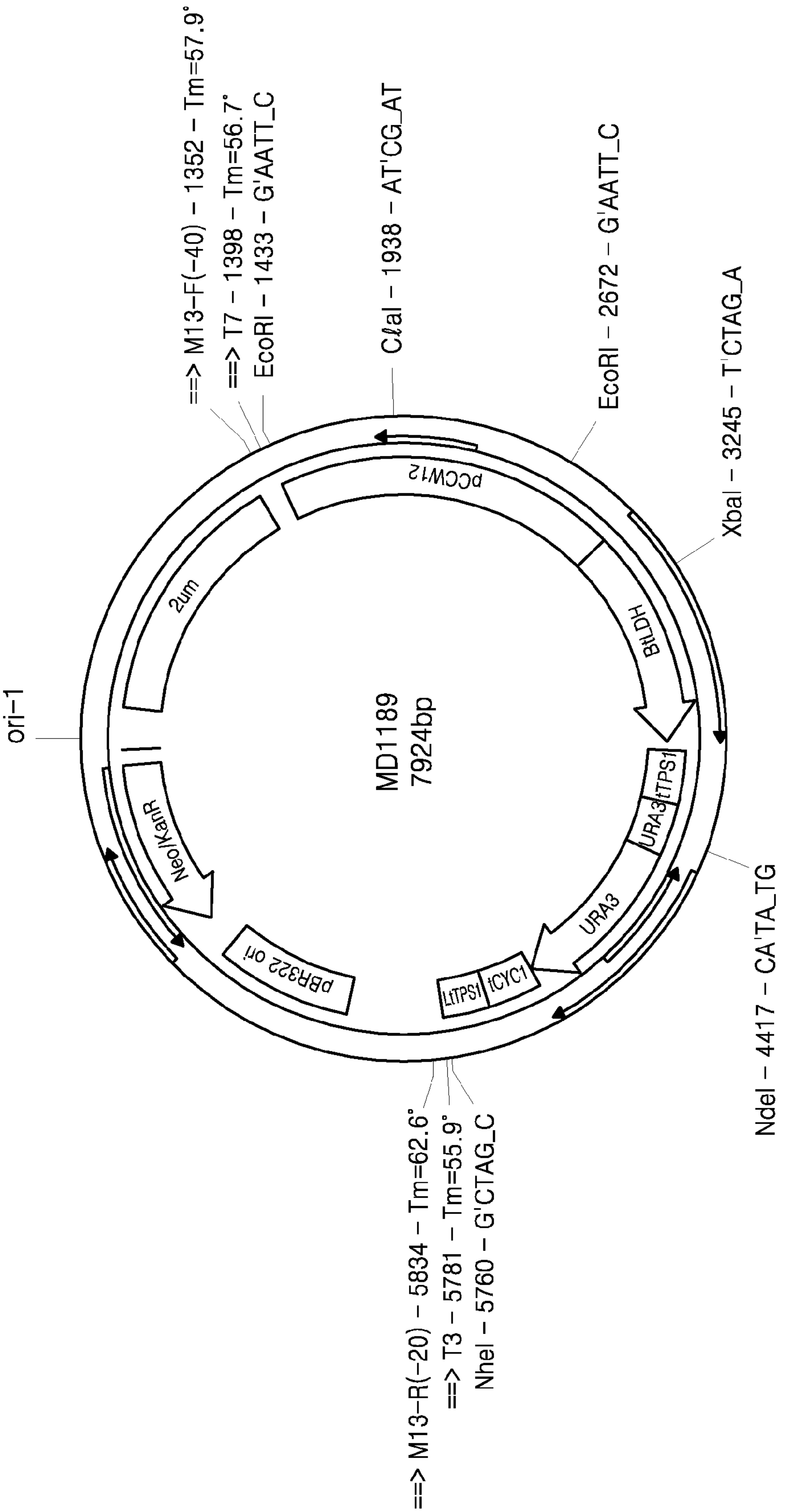
FIG. 9 is a schematic illustration of a MD1189 vector.

PCR was performed with a primer set of SEQ ID NOS: 44 and 45 as primers to obtain a 1,039 bp DNA fragment from the pRS416-CCW12p-BtLDH or pRS416-CCW12p-BtLDH (D236G) prepared in Example 1. The DNA fragment thus obtained was mixed with a MD0922 vector digested with KpnI and SacI, cloned by using an in-fusion kit, introduced to TOP10 (Invitrogen), which is an *E. coli* strain, by using a general heatshock transformation method, and spread on a LB agar plate including 50 ug/ml of kanamycin (including 10 g/L of Bacto Tryptone, 5 g/L of yeast extract, 10 g/l of sodium chloride, 15 g/L of Bacto agar, and 50 ug/ml of kanamycin). Plasmid was collected from the colonies grown for 10 hours at 37° C. collected by using a general alkaline lysis miniprep method, and vectors such as SEQ ID NO: 46 or SEQ ID NO: 47 among the plasmid were selected to obtain a MD1188 vector or a MD1189 vector, which is a yeast LDH overexpression vector. FIG. 8 is a schematic view of the MD1188 vector. The MD1188 vector is a vector is prepared by cloning a wild-type BtLDH gene. FIG. 9 is a schematic view of the MD1189 vector. The MD1189 vector is a vector is prepared by cloning a BtLDH (D236G) gene.

2.2.3 Preparation of Strain in which L-LDH Expression Cassette is Introduced as Pyruvate Decarboxylase (pdc1) Gene is Deleted PCR was performed with a genomic DNA of a *S. cerevisiae* CEN.PK2-1D natural-type strain as a template and a primer set of SEQ ID NOS: 48 and 49 as primers to obtain a 260 bp DNA fragment. Also, PCR was performed with the same genomic DNA as a template and a primer set of SEQ ID NOS: 50 and 51 as primers to obtain a 257 bp DNA fragment. Also, PCR was performed with the MD1188 vector or the MD1189 vector prepared in Example 2.2.2 as a template and a primer set of T7 primers and T3 primers as primers to obtain a 4,422 bp DNA fragment. The 260 bp, 257 bp, and 4,422 bp DNA fragments thus obtained were all mixed together, and PCR was performed with a primer set of SEQ ID NOS: 48 and 51 as primers to obtain a 4,881 bp or 4,881 bp DNA fragment.

The DNA fragment thus obtained was transformed into the MD1192 strain prepared in Example 2.2.1, and strains grown in a minimal medium free of uracil (SD-URA; including 6.7 g of yeast nitrogen base, 1.92 g of synthetic drop-out without uracil, 20 g of D-glucose, and 20 g/L of Bacto agar) were isolated. On a wild-type strain among the isolated strains, PCR was performed with a primer set of SEQ ID NOS: 52 and 53 in which a 2,904 bp DNA fragment was confirmed as primers to secure a strain in which a 5,414 bp DNA fragment was confirmed. The secured strain was seed cultured in a YPD agar plate (including 10 g of yeast extract, 20 g of Bacto Peptone, and 20 g/L of D-glucose) for one day, spread on a 5-FOA plate (including 6.7 g of yeast nitrogen base, 1.92 g of synthetic drop-out without uracil, 0.1 g of uracil, 20 g of D-glucose, 1 g of 5-fluoroorotic acid, and 20 g/L of Bacto agar), and strains grown from the medium were isolated. On the isolated strains, PCR was performed with a primer set of SEQ ID NOS: 52 and 53 as primers to secure a strain in which a 4,020 bp DNA fragment was confirmed. Among the strains, the strain strated from the MD1188 vector was a *S. cerevisiae* CEN.PK2-1D (Δpdc1Δcyb2+$BtLDH_w$) strain, and the strain strated from the MD1189 vector was a *S. cerevisiae* CEN.PK2-1D (Δpdc1Δcyb2+BtLDH(D236G) strain.

Example 2.3

Preparation of Strain in which L-LDH Expression Vector is Introduced to *S. cerevisiae* from which PDC1 is Deleted Each of the pRS416-CCW12p-BtLDH(N108G) and pRS416-CCW12p-BtLDH(N108L) prepared in Example 2 was inserted into the *S. cerevisiae* CEN.PK2-1D (△ PDC1) strain deleted of PDC1 in Example 4 in the manner described as follows.

pRS416-CCW12p-BtLDH(N108G) prepared in Example 2 was mixed with 50% polyethylene glycol and single stranded carrier DNA, reacted in a water bath at a temperature of 42° C. for 1 hour, and a culture medium obtained therefrom was spreaded onto a uracil free minimum solid medium (YSD, 6.7 g/L yeast nitrogen base without amino acids, 1.4 g/L Amino acid dropout mix (-ura)), and then cultured at a temperature about 30° C. for about 24 hours or more.

Eight colonies (mutant strains) grown on the plate were selected, again patched onto a YSD (-ura) solid medium, and, at the same time, cultured in a YSD (-ura) liquid medium, and then a commercial kit (Yeast plasmid isolation kit, Clontech) was used to isolate plasmid DNA. The plasmid DNA separated therefrom was used as a template, primers of SEQ ID NO: 62 and 63 were used to perform PCR to identify a plasmid including BtLDH(N108G), and PCR products obtained therefrom were electrophoresed to confirm that the plasmid inserted was pRS416-CCW12-BtLDH(N108G). As a result, *S. cerevisiae* CEN.PK2-1D (△ PDC1+BtLDH(N108G)) was obtained.

Additionally, the pRS416-CCW12p-BtLDH(N108L) prepared in Example 2 was mixed with 50% polyethylene glycol and single stranded carrier DNA, reacted in a water bath at a temperature of 42° C. for 1 hour, and a culture medium obtained therefrom was spreaded onto a uracil free minimum solid medium (YSD, 6.7 g/L yeast nitrogen base without amino acids, 1.4 g/L Amino acid dropout mix (-ura)), and then cultured at a temperature about 30° C. for about 24 hours or more to obtain *S. cerevisiae* CEN.PK2-1D (△ PDC1+BtLDH(N108L)). Additionally, the pRS416-CCW12p-BtLDHwt prepared in Example 2 was transformed in *S. cerevisiae* CEN.PK2-1D (△ PDC1) in the same manner as described above to obtain *S. cerevisiae* CEN.PK2-1D (△ PDC1+BtLDHwt).

Example 3

Evaluation of Lactate Productivity by Using *S. cerevisiae* Strain in which Lactate Dehydrogenase Mutant is Introduced 3.1 Evaluation of Lactate Productivity of *S. cerevisiae* CEN.PK2-1D (△ PDC1+BtLDH(E102G)) Strain, *S. cerevisiae* CEN.PK2-1D (△ PDC1+BtLDH(D236G)) Strain, and *S. cerevisiae* CEN.PK2-1D (△ PDC1+BtLDH (S237G)) Strain

*S. cerevisiae* strains including the wild-type BtLDH, BtLDH(E102G), BtLDH(D236G), and BtLDH(S237G) vectors prepared in Example 2.1.3 were each inoculated into 50 ml of a minimal Ura drop-out media containing 4% or glucose so that an $OD_{600}$ value was 1, and cultured under a microaerobic condition for 48 hours while stirring at a rate of about 90 rpm at 30° C. The $OD_{600}$ value was measured by using a spectrophotometer. A concentration of lactate was analyzed by using a high performance liquid chromatography (HPLC).

TABLE 3

| | V | W | A98G | E102G | N108G | S167G | M174G | D236G | S237G |
|---|---|---|---|---|---|---|---|---|---|
| Concentration of lactate (g/L) | 0.0 | 7.4 | 5.7 | 8.8 | 10.4 | 4.5 | 6.6 | 12.7 | 10.5 |

Table 3 shows the concentrations of lactate produced by the *S. cerevisiae* strains including the wild-type BtLDH, BtLDH(E102G), BtLDH(D236G), and BtLDH(S237G) vectors, each respectively. As shown in Table 3, the *S. cerevisiae* CEN.PK2-1D (△ PDC1+BtLDH(E102G)) strain in which a BtLDH(E102G) expression vector was introduced had about 8.8 g/L of lactate production which was an increased amount of lactate production compared to about 7.4 g/L of lactate production of the *S. cerevisiae* CEN.PK2-1D (△ PDC1+BtLDHw) strain, in which a wild-type BtLDH was introduced.

Also, the *S. cerevisiae* CEN.PK2-1D (△ PDC1+BtLDHw) strain, in which a wild-type BtLDH was introduced, had about 12.7 g/L of lactate production which was an increased amount of lactate production compared to that of the *S. cerevisiae* CEN.PK2-1D (△ PDC1+BtLDHw) strain, in which a wild-type BtLDH was introduced.

Also, the *S. cerevisiae* CEN.PK2-1D (△ PDC1+BtLDH (S237G)) strain, in which a BtLDH(S237G) expression vector was introduced, had about 10.5 g/L of lactate production which was an increased amount of lactate production compared to that of the *S. cerevisiae* CEN.PK2-1D (△ PDC1+BtLDHw) strain, in which a wild-type BtLDH was introduced.

3.2 Evaluation of Lactate Production of *S. cerevisiae* CEN.PK2-1D (△ PDC1 △ CYB2+BtLDH(D236G)) Strain A *S. cerevisiae* strain including the wild-type BtLDH and BtLDH(D236G) vectors prepared in Example 2.2.3 were each inoculated into 50 ml of YPD liquid medium (including 10 g/L of yeast extract, 20 g/L of Bacto Peptone, and 80 g/L of D-glucose) so that an $OD_{600}$ value was 1, and cultured under a microaerobic condition for 48 hours while stirring at a rate of about 90 rpm at 30° C. The $OD_{600}$ value was measured by using a spectrophotometer. A concentration of lactate was analyzed by using a high performance liquid chromatography (HPLC).

TABLE 4

| | Concentration of lactate (g/L) | Yield (g/g %) |
|---|---|---|
| Wild-type BtLDH | 16.8 ± 0.4 | 31.3 ± 1 |
| BtLDH(D236G) | 18.2 ± 0.4 | 36.6 ± 0.8 |

Table 4 shows concentrations of lactate produced by the *S. cerevisiae* strains including the wild-type BtLDH and BtLDH(D236G) vectors. As shown in Table 4, an amount of lactate production of the *S. cerevisiae* CEN.PK2-1D (△ PDC1 △ CYB2+BtLDH(D236G)) strain, in which a BtLDH(D236G) expression cassette was introduced, was about 18.2 g/L which was about 8.33% increased amount compared to about 16.8 g/L of an amount of lactate production of the *S. cerevisiae* CEN.PK2-1D (△ PDC1 △ CYB2+BtLDHw) strain, in which a wild-type BtLDH cassette was introduced. Also, the *S. cerevisiae* CEN.PK2-1D (△ PDC1 △ CYB2+BtLDH(D236G)) strain had a lactate production yield of about 36.6 g/g % which was about 16.9% improved lactate production yield compared to the *S. cerevisiae* CEN.PK2-1D (△ PDC1 △ CYB2+ BtLDHw) strain, in which a wild-type BtLDH cassette was introduced, which had a lactate production yield of about 31.3 g/g %. The production yield was calculated by (amount of lactate production (g)/amount of glucose uptake (g))×100.

3.3 Evaluation of Lactate Productivity of *S. cerevisiae* CEN.PK2-1D (△ PDC1 △ CYB2+BtLDH(D236G)) Strain Under pH 3.0 Condition

*S. cerevisiae* strains including the wild-type BtLDH and BtLDH(D236G) vectors prepared in Example 2.2.3 were each inoculated into 50 ml of YPD liquid medium, containing lactate and of which pH was adjusted to 3.0, (including 10 g/L of yeast extract, 20 g/L of Bacto Peptone, 80 g/L of D-glucose, and 20 g/L of lactate) so that an $OD_{600}$ value was 1, and cultured under a microaerobic condition for 48 hours while stirring at a rate of about 90 rpm at 30° C. The $OD_{600}$ value was measured by using a spectrophotometer. A concentration of lactate was analyzed by using a high performance liquid chromatography (HPLC).

TABLE 5

| | Concentration of lactate (g/L) | Yield (g/g %) |
|---|---|---|
| Wild-type BtLDH | 31.4 | 28.3 |
| BtLDH(D236G) | 34.9 | 32.8 |

Table 5 shows concentrations of lactate produced by the *S. cerevisiae* strains including the wild-type BtLDH and BtLDH(D236G) vectors. As shown in Table 5, an amount of lactate production of the *S. cerevisiae* CEN.PK2-1D (△ PDC1 △ CYB2+BtLDH(D236G)) strain, in which a BtLDH(D236G) expression cassette was introduced, was about 34.9 g/L which was an increased amount compared to about 31.4 g/L of an amount of lactate production of the *S. cerevisiae* CEN.PK2-1D (△ PDC1 △ CYB2+BtLDHw) strain, in which a wild-type BtLDH cassette was introduced. Also, the *S. cerevisiae* CEN.PK2-1D (△ PDC1 △ CYB2+BtLDH(D236G)) strain had a lactate production yield of about 32.8 g/g % which was an improved lactate production yield compared to the *S. cerevisiae* CEN.PK2-1D (△ PDC1 △ CYB2+BtLDHw) strain, in which a wild-type BtLDH cassette was introduced, which had a lactate production yield of about 28.3 g/g %.

Therefore, it was conformed that a *S. cerevisiae* strain including the BtLDH(D236G) vector may produce a large amount of lactate and may produce lactate at a high yield even under an acid condition, for example, at pH of 3.0, compared to those of a *S. cerevisiae* strain including a wild-type BtLDH vector, a control group.

Example 3.4

Producing L-lactate by Using a *S. cerevisiae* Strain Inserted with L-LDH Mutant The wild-type prepared in Example 2.3 and *S. cerevisiae* CEN.PK2-1D strains including BtLDH(N108G) and BtLDH(N108L) mutants were spreaded onto YSD (-ura) solid medium to culture the same at a temperature of 30 for 24 hours or more and then inoculated in 50 ml of YSD (-ura) including 40 g/L of glucose to culture the same under an aerobic condition at a temperature of 30° C. for 16 hours.

Fermentation was performed by measuring an amount of cell concentration in 50 ml of culture medium when an optical density (OD) at 600 nm reached about 5.0 by using a spectrophotometer, centrifuging the cells, discarding a supernatant obtained therefrom, and resuspending the cells, and then inoculating the cells again in about 50 ml of new YSD (-ura) including about 40 g/L of glucose. The cells were cultured in a stirring incubator while maintaining a speed of about 90 rpm at a temperature of about 30° C. for about 8 hours to ferment the cells. 80 g of glucose was initially provided. After about 17 hours, at which point the cells had consumed almost all of the glucose that was initially provided, a sample was periodically extracted from a flask during fermentation. The extracted sample was centrifuged at about 13,000 rpm for about 10 minutes, and then concentrations of lactate, glycerol, and ethanol were analyzed by using high performance liquid chromatography (HPLC). Yield is shown as a percentage of a value obtained by dividing lactate (g) by the amount of glucose that was initially provided (g).

As shown in Table 6, the *S. cerevisiae* CEN.PK2-1D (△ PDC1+BtLDH(N108G)) strain inserted with a BtLDH (N108G) expression vector showed productivity of about 10.97 g/L and a yield of 13.49%, and thus, showed improved lactate productivity and yield compared to a strain inserted with the wild-type L-LDH(BtLDH). Additionally, the strain showed low productivity of glycerol and ethanol.

Additionally, the *S. cerevisiae* CEN.PK2-1D (△ PDC1+ BtLDH(N108L)) strain inserted with a BtLDH(N108L) expression vector showed productivity of about 10.10 g/L and yield of 12.55%, and thus, showed improved lactate productivity and yield compared to a strain inserted with the wild-type L-LDH(BtLDH). Additionally, the strain showed low productivity of glycerol and ethanol.

TABLE 6

| Vector inserted into *S. cerevisiae* CEN.PK2-1D (△ PDC1) strain | lactate (g/L) | Yield % (g/g) | Glycerol (g/L) | EtOH (g/L) |
|---|---|---|---|---|
| btLDH wild-type | 9.40 | 11.68 | 2.31 | 32.28 |
| btLDH(N108G) | 10.97 | 13.49 | 2.15 | 31.23 |
| btLDH(N108L) | 10.10 | 12.55 | 2.08 | 31.67 |

Example 4

Evaluation of Lactate Dehydrogenase Mutant Activity (4.1) Evaluation of BtLDH(N108G) and BtLDH(N108L) Activity The wild-type lactate dehydrogenase prepared in Example 2.3 and a mutant expression vector thereof were expressed in *E. coli* having a histidine tag and then purified by using TALON® metal affinity resin (Clontech, Inc.). Thereafter, specific activity of the wild-type lactate dehydrogenase and the mutant thereof were measured, the results of which are shown in Table 3. Additionally, Km and Kcat of btLDH(N108G) that showed high lactate productivity in Example 3.4 were measured, the results of which are shown in Table 7. The specific activity, Km, and Kcat were measured according to the method described in Microbiology 1994 140:2077-2084.

As shown in Table 7, the specific activity of BtLDH (N108G) was about 0.167 U/mg at pH 7.5, thus showing that the specific activity increased by about 24.6% compared to the specific activity of the wild-type BtLDH, which was the control group. Additionally, the specific activity of BtLDH (N108L) was about 0.156 U/mg at pH 7.5, thus showing that the specific activity increased by about 11.6% compared to the wild-type BtLDH, which was the control group. Additionally, the lactate dehydrogenase BtLDH(N108G) showed higher specific activity at low pH such as pH of 5.2, and showed smaller amount of change in specific activity compared to a change in specific activity of the wild-type lactate dehydrogenase with respect to a change in pH.

TABLE 7

| Enzyme | Specific activity (U/mg, pH 7.5) |
|---|---|
| Wild-type BtLDH | 0.134 |
| BtLDH(N108G) | 0.167 |
| BtLDH(N108L) | 0.156 |

Additionally, as shown in Table 8, Km and Kcat of BtLDH(N108G) were respectively about 0.48 mM and about 2279/min, which are respectively about 4.36 times as great and about 2.76 times as great as Km and Kcat of the wild-type BtLDH, which was the control group.

TABLE 8

| Enzyme | Km (mM) | Kcat (/min) |
|---|---|---|
| Wild-type BtLDH | 0.11 | 826 |
| BtLDH(N108G) | 0.48 | 2279 |

(4.2) Specific Activity Evaluation of Lactate Dehydrogenase Mutant

The *S. cerevisiae* CEN.PK2-1D (△ PDC1+BtLDHw) and *S. cerevisiae* CEN.PK2-1D (△ PDC1+BtLDH (E102G)) strains prepared in Examples 2.2.3 were disrupted, and a wild-type lactate dehydrogenase and a lactate dehydrogenase mutant from the obtained crude extract were each purified by using TALON® metal affinity resin (Clontech, Inc.). Then, specific activities of the wild-type lactate dehydrogenase and a mutant thereof were measured, and the results are shown in Table 9. Table 9 shows specific activities of the wild-type lactate dehydrogenase and the lactate dehydrogenase mutant. As shown in Table 9, a specific activity of the BtLDH(D236G) vector was about 0.635 U/mg which was higher than a specific activity of a wild-type BtLDH having a value of about 0.241 U/mg.

TABLE 9

| | Specific activity (U/mg) |
|---|---|
| Wild-type BtLDH | 0.241 |
| BtLDH(D236G) | 0.635 |

As described above, according to the one or more of the above embodiments of the present invention, a lactate dehydrogenase mutant, a polynucleotide coding for the lactate dehydrogenase mutant, a vector including the polynucleotide, and a yeast cell including the polynucleotide may be used to provide increased lactate productivity compared to a suitable control.

According to a method of preparing a lactate dehydrogenase mutant, a mutant having efficient lactate productivity may be prepared.

According to a method of preparing lactate, lactate may be produced efficiently.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant yeast cell comprising an exogenous polynucleotide encoding a lactate dehydrogenase that converts pyruvate into lactate, wherein the lactate dehydrogenase comprises SEQ ID NO: 1 including one or more of the following mutations:E102G, N108G, N108L, D236G, or S237G.

2. The recombinant yeast cell of claim 1, wherein the lactate dehydrogenase has the amino acid sequence of SEQ ID NO: 3, 4, 5, 54, or 55.

3. The recombinant yeast cell of claim 1 comprising disruption of a gene encoding a polypeptide that converts pyruvate into acetaldehyde.

4. The recombinant yeast cell of claim 3, wherein the polypeptide that converts pyruvate into acetaldehyde has the amino acid sequence of SEQ ID NO: 9.

5. The recombinant yeast cell of claim 3, wherein the gene encoding the polypeptide that converts pyruvate into acetaldehyde has the nucleotide sequence of SEQ ID NO: 11.

6. The recombinant yeast cell of claim 3 further comprising disruption of a gene encoding a polypeptide that converts lactate into pyruvate.

7. The recombinant yeast cell of claim 6, wherein the polypeptide that converts lactate into pyruvate comprises the amino acid of SEQ ID NO: 10.

8. The recombinant yeast cell of claim 6, wherein the gene encoding a polypeptide that converts lactate into pyruvate has the nucleotide sequence of SEQ ID NO: 12.

9. The recombinant yeast cell of claim 1, wherein the recombinant yeast cell belongs to *Saccharomyces, Kluyveromyces, Candida, Pichia, Issatchenkia, Debaryomyces, Zygosaccharomyces*, or *Saccharomycopsis* genus.

10. The recombinant yeast cell of claim 1, wherein the recombinant yeast cell belongs to *Saccharomyces cerevisiae.*

11. A method of producing lactate, the method comprising culturing the recombinant yeast cell of claim 1 to produce lactate; and collecting lactate from the culture.

* * * * *